US012614616B2

(12) United States Patent
Compas et al.

(10) Patent No.: US 12,614,616 B2
(45) Date of Patent: *Apr. 28, 2026

(54) WORKFLOW FOR AUTOMATIC MEASUREMENT OF DOPPLER PIPELINE

(71) Applicant: INTERNATIONAL BUSINESS MACHINES CORPORATION, Armonk, NY (US)

(72) Inventors: Colin Compas, San Jose, CA (US); Yaniv Gur, San Jose, CA (US); Mehdi Moradi, San Jose, CA (US); Mohammadreza Negahdar, San Jose, CA (US); Tanveer Syeda-Mahmood, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/492,163

(22) Filed: Oct. 1, 2021

(65) Prior Publication Data
US 2022/0028507 A1 Jan. 27, 2022

Related U.S. Application Data

(63) Continuation of application No. 15/295,847, filed on Oct. 17, 2016, now Pat. No. 11,177,022.

(51) Int. Cl.
*G16H 10/60* (2018.01)
*G06F 18/2413* (2023.01)
(Continued)

(52) U.S. Cl.
CPC ....... *G16H 10/60* (2018.01); *G06F 18/24143* (2023.01); *G06Q 10/0633* (2013.01);
(Continued)

(58) Field of Classification Search
CPC ........ G16H 10/60; G16H 30/20; G16H 50/20; G06K 9/00; G06K 9/0053; G06K 9/6274;
(Continued)

(56) References Cited

U.S. PATENT DOCUMENTS 4,770,184 A 9/1988 Greene, Jr. et al.
5,638,823 A 6/1997 Akay et al.
(Continued)

FOREIGN PATENT DOCUMENTS

CN 105574337 A 5/2016
EP 2628113 A1 8/2013
(Continued)

OTHER PUBLICATIONS

Syeda-Mahmood et al., "Shape-based similarity retrieval of doppler images for clinical decision support," IEEE: 855-862 (2010).
(Continued)

*Primary Examiner* — Michael I Ezewoko
*Assistant Examiner* — William T. Monticello
(74) *Attorney, Agent, or Firm* — Seed Intellectual Property Law Group LLP

(57) ABSTRACT

Workflows for automatic measurement of Doppler is provided. In various embodiments, a plurality of frames of a medical video are read. A mode label indicative of a mode of each of the plurality of frames is determined. At least one of the plurality of frames is provided to a trained feature generator. The at least one of the plurality of frames have the same mode label. At least one feature vector is obtained from the trained feature generator corresponding to the at least one of the plurality of frames. At least one feature vector is provided to a trained classifier. A valve label indicative of a valve is obtained from the trained classifier corresponding to the at least one of the plurality of frames. One or more measurement is extracted indicative of a
(Continued)

disease condition from those of the at least one of the plurality of frames matching a predetermined valve label.

15 Claims, 22 Drawing Sheets

(51) Int. Cl.

| | |
|---|---|
| *G06N 3/045* | (2023.01) |
| *G06N 3/08* | (2023.01) |
| *G06N 5/01* | (2023.01) |
| *G06N 20/10* | (2019.01) |
| *G06N 20/20* | (2019.01) |
| *G06Q 10/0633* | (2023.01) |
| *G06V 10/82* | (2022.01) |
| *G06V 20/62* | (2022.01) |
| *G06V 30/10* | (2022.01) |
| *G06V 30/19* | (2022.01) |
| *G16H 30/20* | (2018.01) |
| *G16H 50/20* | (2018.01) |

(52) U.S. Cl.
CPC ........ *G06V 10/82* (2022.01); *G06V 30/19173* (2022.01); *G16H 30/20* (2018.01); *G16H 50/20* (2018.01); *G06F 2218/10* (2023.01); *G06N 3/045* (2023.01); *G06N 3/08* (2013.01); *G06N 5/01* (2023.01); *G06N 20/10* (2019.01); *G06N 20/20* (2019.01); *G06V 20/635* (2022.01); *G06V 30/10* (2022.01); *G06V 2201/03* (2022.01)

(58) Field of Classification Search
CPC .... G06Q 10/0633; G06N 20/20; G06N 20/10; G06N 3/0454; G06N 3/08; G06N 5/003; G06V 30/10; G06V 2201/03; G06V 20/635
See application file for complete search history.

(56) References Cited

U.S. PATENT DOCUMENTS

| | | | |
|---|---|---|---|
| 6,574,629 | B1 | 6/2003 | Cooke, Jr. et al. |
| 6,674,879 | B1 | 1/2004 | Weisman et al. |
| 6,915,254 | B1 | 7/2005 | Heinze et al. |
| 7,672,497 | B2 | 3/2010 | Nicponski |
| 7,738,683 | B2 | 6/2010 | Cahill et al. |
| 8,280,750 | B2 | 10/2012 | Krishnan et al. |
| 9,122,773 | B2 | 9/2015 | Li et al. |
| 10,169,871 | B2 | 1/2019 | Hibbard et al. |
| 11,177,022 | B2 | 11/2021 | Compas et al. |

| | | | |
|---|---|---|---|
| 2001/0053986 | A1 | 12/2001 | Dick |
| 2003/0104470 | A1 | 6/2003 | Fors et al. |
| 2005/0020903 | A1 | 1/2005 | Krishnan et al. |
| 2005/0038342 | A1 | 2/2005 | Mozayeni et al. |
| 2007/0150025 | A1 | 6/2007 | Dilorenzo et al. |
| 2008/0208630 | A1 | 8/2008 | Fors et al. |
| 2008/0242996 | A1 | 10/2008 | Hall et al. |
| 2010/0217094 | A1 | 8/2010 | Seward |
| 2010/0240996 | A1* | 9/2010 | Ionasec et al. |
| 2011/0125531 | A1 | 5/2011 | Seare et al. |
| 2011/0184759 | A1 | 7/2011 | Selker et al. |
| 2012/0020563 | A1 | 1/2012 | Amir et al. |
| 2012/0221347 | A1 | 8/2012 | Reiner |
| 2012/0250957 | A1* | 10/2012 | Syede-Mahmood et al. |
| 2012/0290324 | A1 | 11/2012 | Ribbing et al. |
| 2012/0321174 | A1 | 12/2012 | Tsymbal et al. |
| 2012/0323606 | A1 | 12/2012 | Ananthasubramaniam et al. |
| 2013/0262357 | A1 | 10/2013 | Amarasingham et al. |
| 2013/0290231 | A1 | 10/2013 | Chbat |
| 2013/0345563 | A1* | 12/2013 | Stuebe et al. |
| 2014/0172456 | A1 | 6/2014 | Qian et al. |
| 2014/0233826 | A1 | 8/2014 | Agaian et al. |
| 2014/0350961 | A1 | 11/2014 | Csurka et al. |
| 2015/0261917 | A1 | 9/2015 | Smith |
| 2015/0272546 | A1* | 10/2015 | Cheon et al. |
| 2016/0026915 | A1 | 1/2016 | Delp |
| 2016/0187199 | A1 | 6/2016 | Brunk et al. |
| 2016/0232658 | A1 | 8/2016 | Syeda-Mahmood |
| 2016/0267226 | A1 | 9/2016 | Xu et al. |
| 2016/0350336 | A1* | 12/2016 | Checka et al. |
| 2017/0018076 | A1 | 1/2017 | Middlebrooks et al. |
| 2018/0053057 | A1* | 2/2018 | De Souza et al. |
| 2018/0101748 | A1 | 4/2018 | Yang et al. |
| 2018/0107787 | A1* | 4/2018 | Compas et al. |
| 2018/0165808 | A1 | 6/2018 | Bagci et al. |
| 2018/0225820 | A1* | 8/2018 | Liang et al. |
| 2018/0259608 | A1 | 9/2018 | Golden et al. |
| 2019/0180136 | A1 | 6/2019 | Bousmalis et al. |
| 2022/0028507 | A1 | 1/2022 | Compas et al. |

FOREIGN PATENT DOCUMENTS

| | | | |
|---|---|---|---|
| WO | 2004-051548 | A2 | 6/2004 |
| WO | 2017/056078 | A1 | 4/2017 |

OTHER PUBLICATIONS

Zhang et al., "Determination of the mean pressure gradient in aortic stenosis by Doppler echocardiography," European Heart Journal, 6:999-1005 (1985).

List of IBM Patents or Patent Applications Treated as Related (Appendix P). Dated Nov. 2, 2021.

* cited by examiner

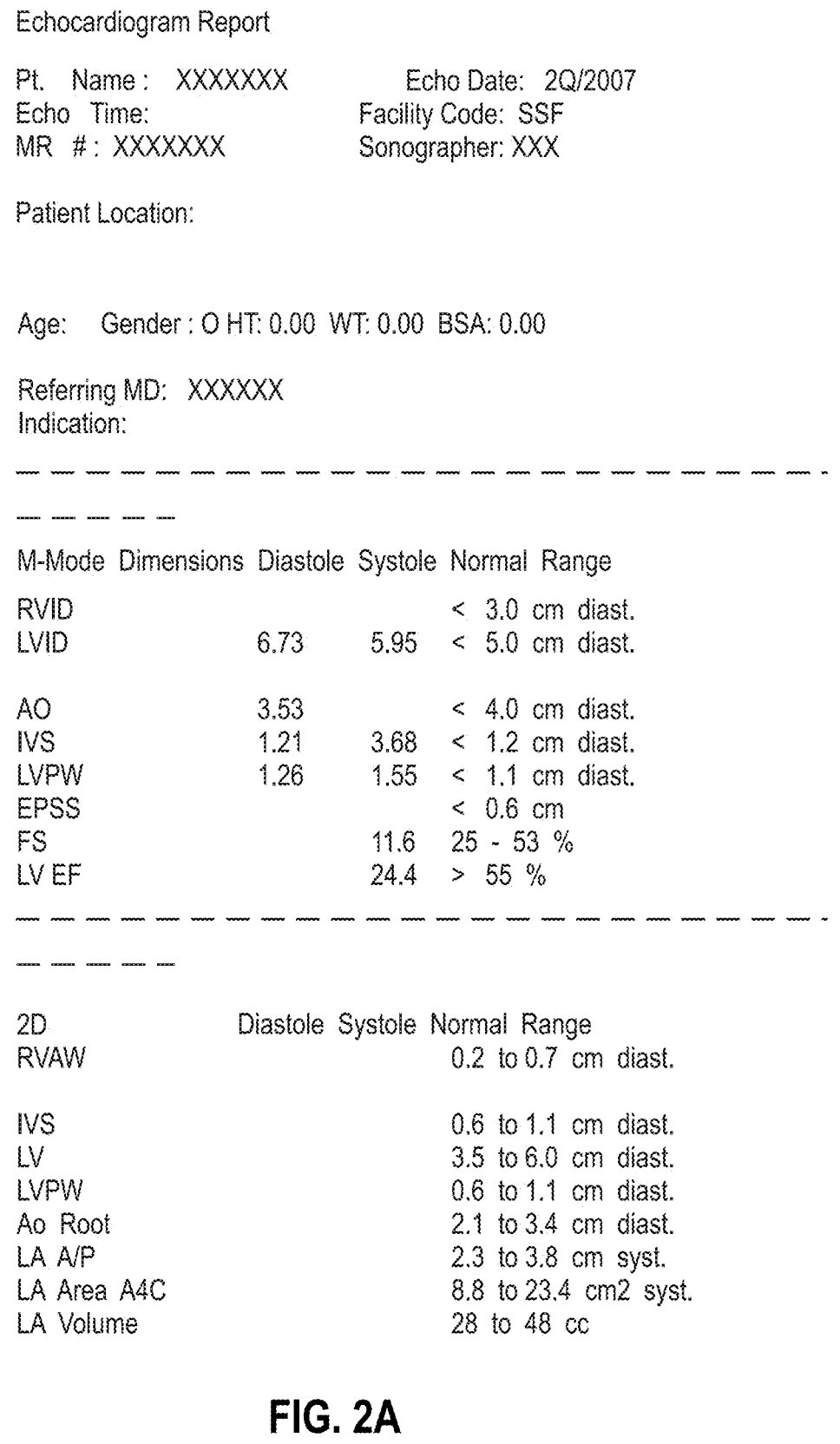

Echocardiogram Report

Pt. Name : XXXXXXX          Echo Date: 2Q/2007
Echo Time:                 Facility Code: SSF
MR # : XXXXXXX             Sonographer: XXX Patient Location:

Age:    Gender : O HT: 0.00  WT: 0.00  BSA: 0.00

Referring MD:  XXXXXX
Indication:

— — — — — — — — — — — — — — — — — — — — — — — — — — — .

— — — — —

| M-Mode Dimensions | Diastole | Systole | Normal Range |
|---|---|---|---|
| RVID | | | < 3.0 cm diast. |
| LVID | 6.73 | 5.95 | < 5.0 cm diast. |
| | | | |
| AO | 3.53 | | < 4.0 cm diast. |
| IVS | 1.21 | 3.68 | < 1.2 cm diast. |
| LVPW | 1.26 | 1.55 | < 1.1 cm diast. |
| EPSS | | | < 0.6 cm |
| FS | | 11.6 | 25 - 53 % |
| LV EF | | 24.4 | > 55 % |

— — — — — — — — — — — — — — — — — — — — — — — — — —  -

— — — — —

| 2D | Diastole | Systole | Normal Range |
|---|---|---|---|
| RVAW | | | 0.2 to 0.7 cm diast. |
| | | | |
| IVS | | | 0.6 to 1.1 cm diast. |
| LV | | | 3.5 to 6.0 cm diast. |
| LVPW | | | 0.6 to 1.1 cm diast. |
| Ao Root | | | 2.1 to 3.4 cm diast. |
| LA A/P | | | 2.3 to 3.8 cm syst. |
| LA Area A4C | | | 8.8 to 23.4 cm2 syst. |
| LA Volume | | | 28 to 48 cc |

FIG. 2A

Figure 3C:
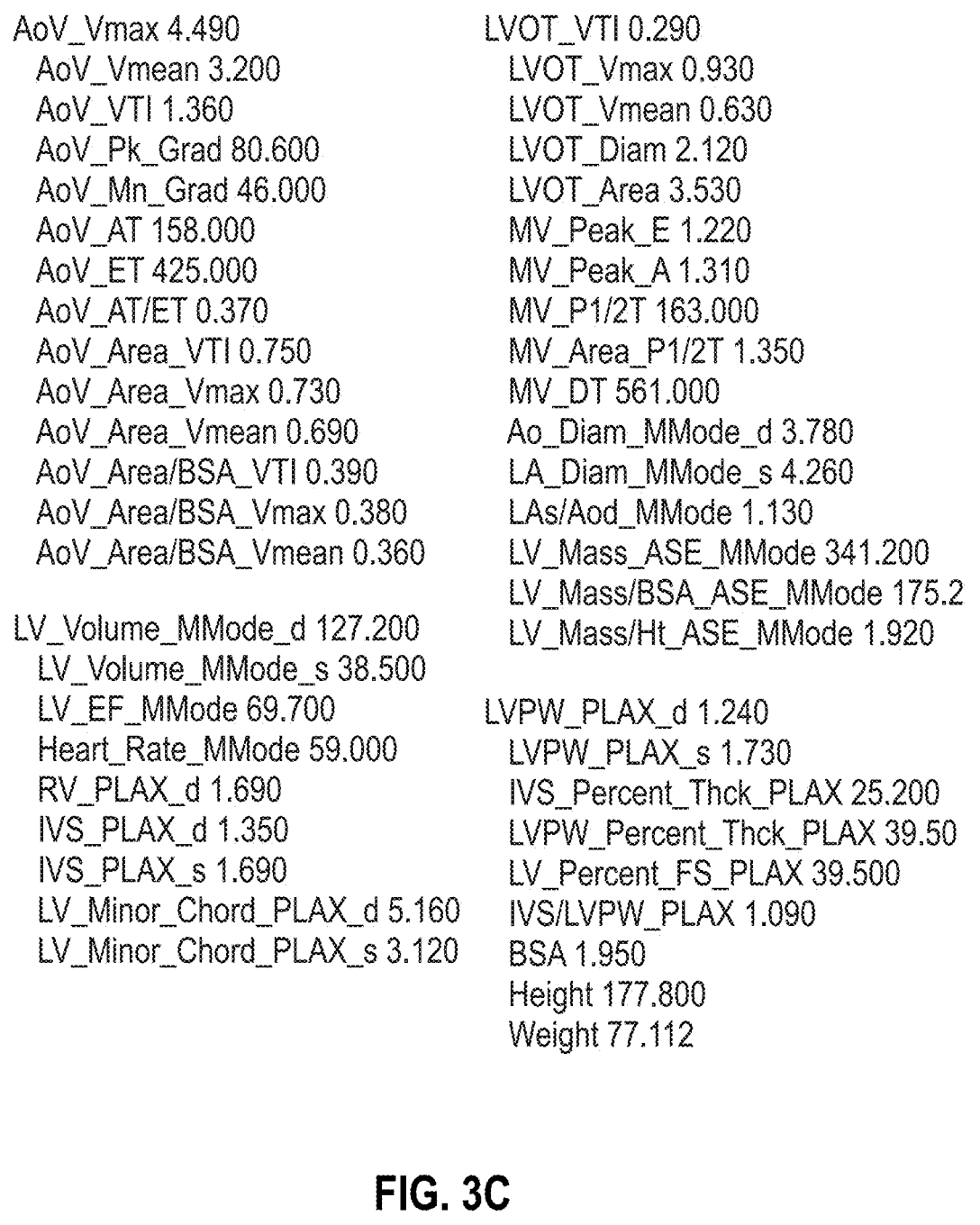

AoV_Vmax 4.490
  AoV_Vmean 3.200
  AoV_VTI 1.360
  AoV_Pk_Grad 80.600
  AoV_Mn_Grad 46.000
  AoV_AT 158.000
  AoV_ET 425.000
  AoV_AT/ET 0.370
  AoV_Area_VTI 0.750
  AoV_Area_Vmax 0.730
  AoV_Area_Vmean 0.690
  AoV_Area/BSA_VTI 0.390
  AoV_Area/BSA_Vmax 0.380
  AoV_Area/BSA_Vmean 0.360

LV_Volume_MMode_d 127.200
  LV_Volume_MMode_s 38.500
  LV_EF_MMode 69.700
  Heart_Rate_MMode 59.000
  RV_PLAX_d 1.690
  IVS_PLAX_d 1.350
  IVS_PLAX_s 1.690
  LV_Minor_Chord_PLAX_d 5.160
  LV_Minor_Chord_PLAX_s 3.120

LVOT_VTI 0.290
  LVOT_Vmax 0.930
  LVOT_Vmean 0.630
  LVOT_Diam 2.120
  LVOT_Area 3.530
  MV_Peak_E 1.220
  MV_Peak_A 1.310
  MV_P1/2T 163.000
  MV_Area_P1/2T 1.350
  MV_DT 561.000
  Ao_Diam_MMode_d 3.780
  LA_Diam_MMode_s 4.260
  LAs/Aod_MMode 1.130
  LV_Mass_ASE_MMode 341.200
  LV_Mass/BSA_ASE_MMode 175.2
  LV_Mass/Ht_ASE_MMode 1.920

LVPW_PLAX_d 1.240
  LVPW_PLAX_s 1.730
  IVS_Percent_Thck_PLAX 25.200
  LVPW_Percent_Thck_PLAX 39.50
  LV_Percent_FS_PLAX 39.500
  IVS/LVPW_PLAX 1.090
  BSA 1.950
  Height 177.800
  Weight 77.112

| Connect to Server | ~ 901 |

| Create Message | ~ 902 |

| Populate Message with Search Keys | ~ 903 |

| Create Attributes for Values Requested | ~ 904 |

| Send Message to Server | ~ 905 |

| Receive Response Messages | ~ 906 |

1000

Read Records ~1001

Extract Features ~1002

Provide Features to Classifier ~1003

Receive Indicator of Disease Condition ~1004

1100

1200

| Read Medical Image | ~1201 |
|---|---|
| Read Measurement Names | ~1202 |
| Apply OCR to Image | ~1203 |
| Generate Template | ~1204 |

1400

Read Frames ~1401

Provide Frames to Feature Generator ~1402

Obtain Feature Vectors ~1403

Provide Feature Vectors to Classifier ~1404

Obtain Valve Label ~1405

Extract Measurements ~1406

1500

| Determine Disease Label | —1501 |

| Retrospective Review | —1502 |

| Identify Earliest Record Reflecting Disease | —1503 |

| Identify Omission or Inconsistency | —1504 |

| Flag Records with Omission or Inconsistency | —1505 |

WORKFLOW FOR AUTOMATIC MEASUREMENT OF DOPPLER PIPELINE

CROSS-REFERENCE TO RELATED APPLICATION

This application claims the benefit of U.S. application Ser. No. 15/295,847, filed Oct. 17, 2016, which is hereby incorporated by reference in its entirety.

BACKGROUND

Embodiments of the present disclosure relate to automatic Doppler measurement, and more specifically, to a workflow for automatic measurement of Doppler.

BRIEF SUMMARY

According to embodiments of the present disclosure, methods of and computer program products for automatic Doppler measurement are provided. A plurality of frames of a medical video are read. A mode label indicative of a mode of each of the plurality of frames is determined. At least one of the plurality of frames is provided to a trained feature generator. The at least one of the plurality of frames have the same mode label. At least one feature vector is obtained from the trained feature generator corresponding to the at least one of the plurality of frames. At least one feature vector is provided to a trained classifier. A valve label indicative of a valve is obtained from the trained classifier corresponding to the at least one of the plurality of frames. One or more measurement is extracted indicative of a disease condition from those of the at least one of the plurality of frames matching a predetermined valve label.

BRIEF DESCRIPTION OF THE SEVERAL VIEWS OF THE DRAWINGS

FIG. 2A is an exemplary echocardiogram report.

FIG. 3C contains exemplary output from an extraction method according to embodiments of the present disclosure.

DETAILED DESCRIPTION

Figure 1:
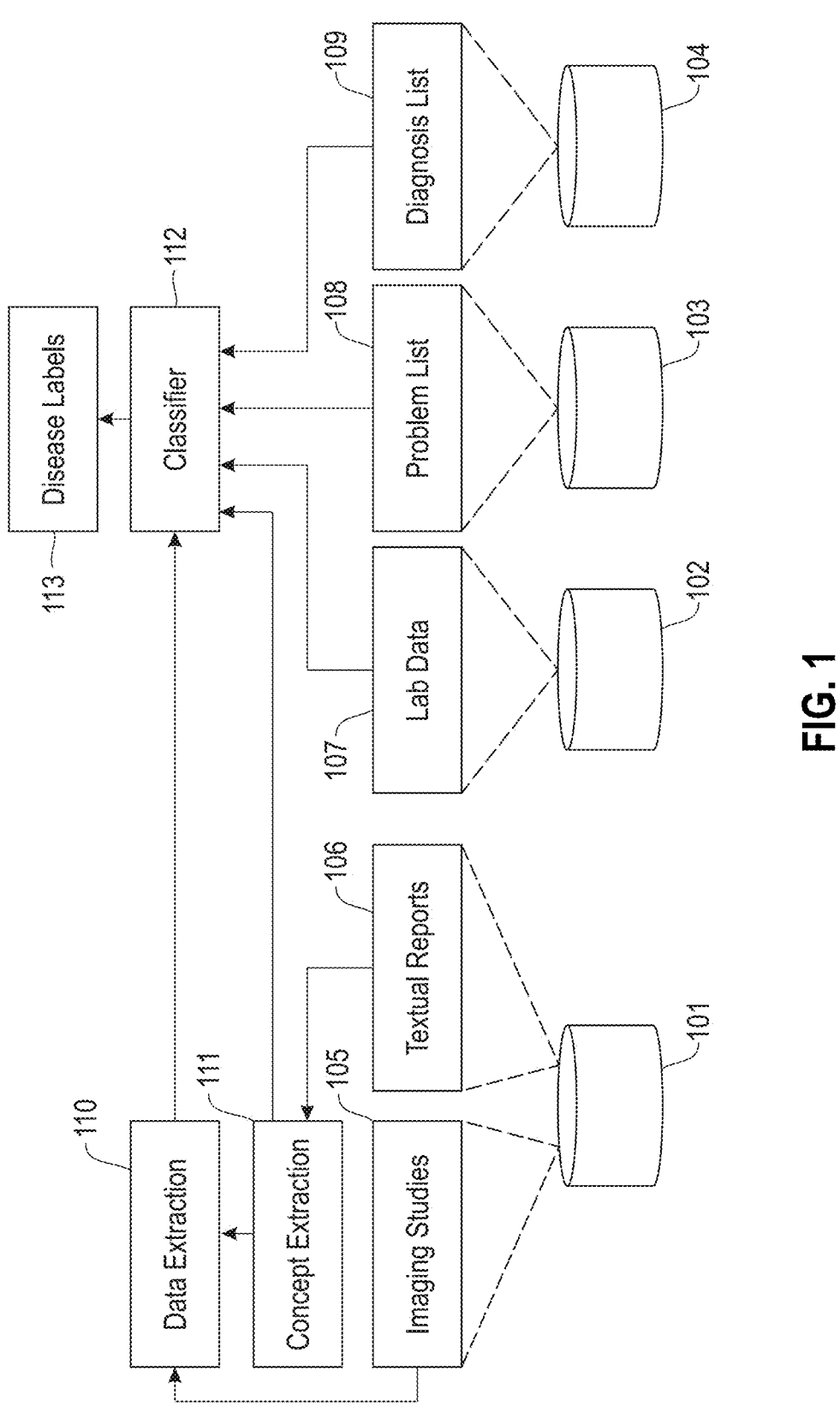
FIG. 1 illustrates a system according to various embodiments of the present disclosure.

With the growth of big data through large electronic health records (EHR), there is an opportunity to leverage medical image analysis in combination with other modality data in EHR to impact the quality of care to patients in a significant way.

Despite the opportunity to record the data in digital electronic records, data entry human errors are quite common in workflow-based electronic health record systems. A billing operator may fail to capture a relevant billing code for a disease by looking at the problem list in an EMR system. A clinician or nurse assistant may fail to put the disease in the problem list of the EMR system by transcribing from the exam's clinical reports. A data entry operator in an imaging facility may fail to transcribe all measurements from the technician into the report. A technician may fail to capture the measurements in the diagnostic study either because he/she was not told to look for the evidence for a disease (possibly because the ordering clinician did not specify this), or because he/she simply forgot to save the measurements or screens on an imaging study in PACS. Any of these errors can ultimately result in a patient not being flagged for a disease. If the disease is one in which sudden death is possible, such as in aortic stenosis, catching such data entry errors through a systematic peer review process can save lives. The present disclosure provides systems and methods for systematically identifying such discrepancies in order to notify the corresponding data entry operator. In various embodiments, this is done by detecting evidence for a disease from multiple information sources, and may include spotting mentions of the disease name in reports, noting the measurements already made by operators that were not flagged, or making new measurements directly from imaging studies.

Accordingly, the present disclosure provides systems and methods for disease detection based on various pre-existing patient data drawn from a variety of different data sources. In particular, the present disclosure provides for the use of medical image analysis in combination with textual and other multimodal data analysis for purposes of identifying patient cohorts at risk for serious diseases such as aortic stenosis.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology reports, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

According to various embodiments of the present disclosure, automated systems and methods for retrospectively predicting patients likely to have disease conditions such as aortic stenosis are provided. In various embodiments, medical image analysis of Doppler patterns is combined with textual content analysis of imaging and reports in a multimodal learning framework. Specifically, evidence of disease conditions such as aortic stenosis may be extracted from sources, such as billable diagnosis, significant problems from EHR, echocardiogram reports, measurements shown on echocardiography video frames, or CW Doppler patterns in echocardiography videos. In some embodiments, disease concepts are identified in echocardiogram reports using a concept extraction algorithm to detect UMLS concept vocabularies and their relevant associated measurements. In some embodiments, measurements captured by echocardiogaphers are reliably extracted through selective image processing and optical character recognition in tabular regions on echocardiogram video frames. In some embodiments, diagnostically relevant measurements for aortic stenosis are automatically extracted from Doppler envelopes using a three step process of relevant Doppler frame identification, envelope tracing and measurement extraction. The frame identification includes classification using convolutional neural network (CNN)-based learned features from Doppler regions. The envelop extraction is made robust by incorporating echocardiographer tracings. In some embodiments, the disease-specific features extracted from each multimodal source of information are combined using a random forest learning formulation to predict patients that are likely to have aortic valve disease.

Referring to FIG. 1, an exemplary system according to embodiments of the present disclosure is illustrated. A variety of data sources 101 . . . 104 contain various patient information. It will be appreciated that the number of data sources is purely exemplary, and that patient information may be spread over an arbitrary number of data sources, connected, for example, via a LAN, WAN, or the internet. Patient data stored in data source 101 . . . 104 may include imaging studies 105, textural report 106, lab data 107, problem list 108, or diagnosis list 109. In some embodiments, imaging studies 105 or other data are located in a PACS. In some embodiments, problem list 108 or other data are located in an EHR system. In various embodiments, imaging studies 105 are subject to measurement or data extraction 110 using various methods set out below to extract data contained in the imagery. In various embodiments, textual reports 106 are subject to concept extraction 111 using various methods set out below to extract clinical concepts. Data resulting from data extraction 110, concept extraction 111, and additional patient data 107 . . . 109 is supplied to a classifier 112. Based on the input features, classifier 112 provides a disease label 113.

The present disclosure provides for identifying patients at risk of various disease conditions such as aortic stenosis by combining medical text and image analysis of medical data such as echocardiogram studies. Such multimodal information may be used for cohort identification. Several embodiments provided herein overlap three inter-disciplinary fields of text analysis, optical character recognition (OCR), and medical image analysis. In various embodiments extraction of clinical concepts from text is provided. In various embodiments, measurements are extracted in addition to disease name mentions for detection of disease conditions. In various embodiments, OCR extraction of clinical measurements from text screens of studies such as echocardiogram studies is provided. Some such embodiments do not rely on manual creation of templates for various manufacturer's echo screens. In various embodiments, reliable extraction of Doppler envelopes is provided, even in the presence of electrocardiogram (ECG) fluctuations during arrhythmia and overlay artifacts in Doppler spectra. In various embodiments, the automatic selection of Doppler frames depicting aortic valves is provided.

Figure 2B:
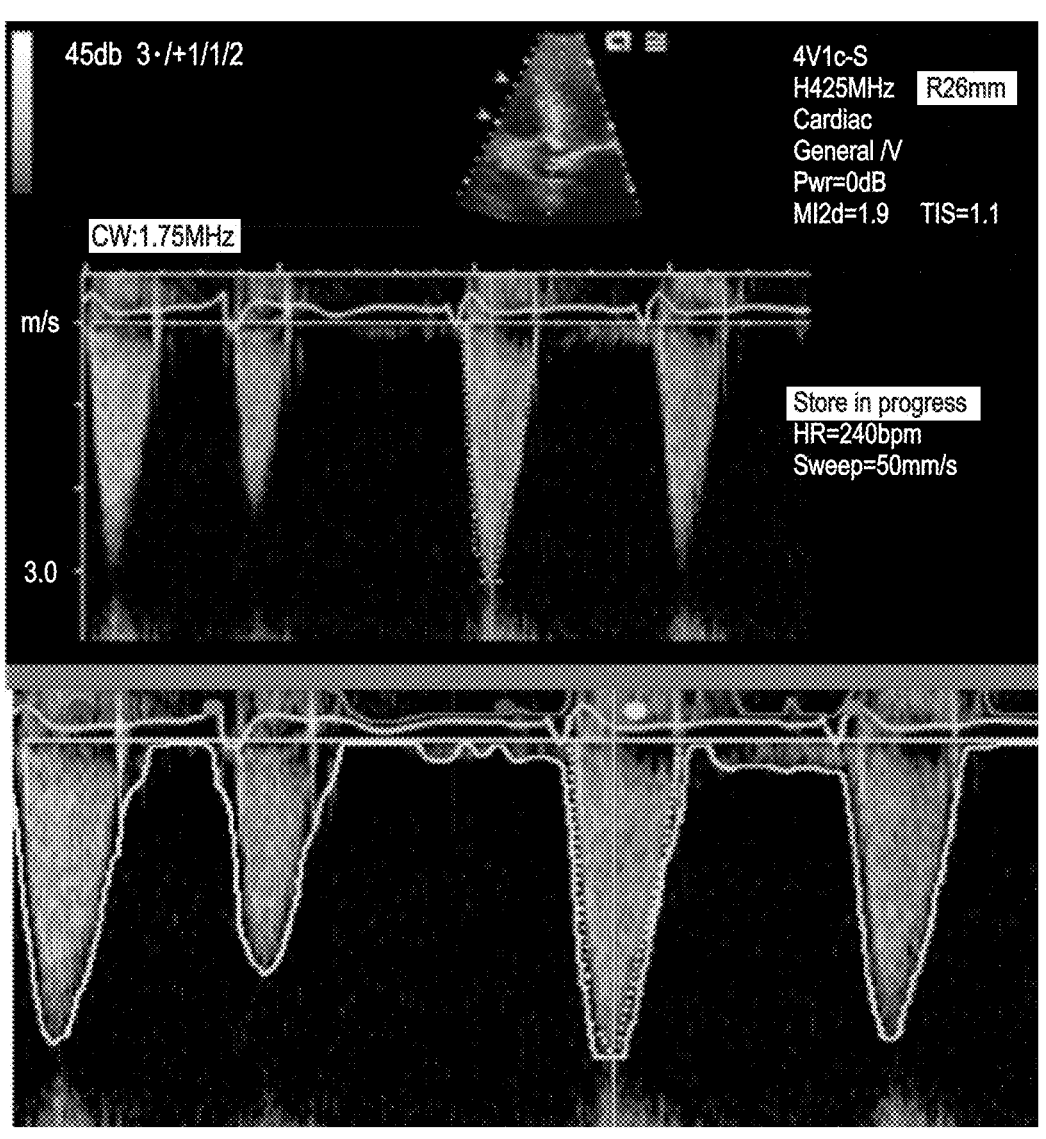
FIG. 2B is an exemplary echocardiogram study.

Various exemplary embodiments provided herein are given with regard to aortic stenosis. However, it will be apparent that the present disclosure is suitable for application to any other disease condition that may be tied to clinical data or observations. Aortic stenosis (AS) is a common heart disease that can result in sudden death. It can be diagnosed through the Doppler patterns in echocardiogram studies such as the exemplary study shown in FIG. 2B. Although the disease can be treated through surgery or transcatheter aortic valve replacements (AVR), it often goes untreated for several reasons. The absence of chest pain and other symptoms may make the disease asymptomatic and not a candidate for detection in echocardiographer's instructions. This together with echocardiographer skill errors can cause a Doppler pattern depicting the disease to be missed entirely. For example, FIG. 2B shows one such case where the echocardiographer missed the evidence for moderate aortic stenosis in the Doppler spectrum. When the relevant measurements are made by the echocardiographer and inserted into the study screens, they may still fail to make it into the overall report. Finally, even if the pattern is detected and makes it into the echocardiogram report, such as the exemplary report in FIG. 2A, pure data entry errors in EHR can leave out the evidence of the disease from a patient record. With thousands of echocardiography studies taken annually, manual peer review is costly and rarely performed, with the result that many patients are going untreated.

Disease Extraction from Reports

In various embodiments of the present disclosure, extraction of evidence of a disease condition from clinical reports is provided. In some exemplary embodiments, the disease condition is aortic stenosis and the clinical report is an echocardiogram report.

To extract evidence of aortic stenosis from echocardiogram reports, a large knowledge graph is generated of over 5.6 million concept terms by combining over 70 reference vocabularies such as SNOMED CT, ICD9, ICD10, RadLex, RxNorm, and LOINC, where its concept nodes are used as vocabulary phrases. The detections of clinical concepts within sentences of the clinical reports uses the longest common subfix (LCF) algorithm. To detect evidence of stenosis, tuples of $\langle D_i, S_j, A_k, V_l \rangle$, are found where $D_i$ are disease name indicators (e.g., "aortic valve disorders," "aortic valve stenosis," etc.), $S_j$ are specific symptoms associated with the disease such as "chest pain," $A_k$ are anatomical abnormalities such as "thickened," "calcified," and $V_l$ are qualifiers such as "mild," "moderate," "severe." These detections are done within neighboring sentences in selected paragraphs where the aortic valve is described in echocardiogram reports.

Next, key measurement names are selected indicating aortic stenosis, such as peak velocity, mean pressure gradient, and aortic valve area. Using their values ranges and units, a measurement name-value pair detector is developed. As the spoken utterances of these names vary in echocardiograms, n-gram analysis is performed of a corpus of over 50,000 reports in a data collection to identify all such significant variants of the measurement names. To detect occurrences of measurement names and their associated values within the context of a detected sentence, the pattern of their occurrences in a sentence is analyzed using part-of-speech (POS) tagging, and dependency graph parsing. For each root concept (e.g., 'gradient'), a chain of its modifiers (in the form of nouns or adjectives, e.g., 'mean trans aortic') are automatically identified from a sentence using an automatic POS tagger. In some embodiments, the automatic POS tagger comprises the Stanford POS tagger. By analyzing thousands of sentences containing the occurrences of measurement vocabulary terms in connection with measurement values and units, regular expression patterns are formed, such a pattern $\langle A \langle \langle B \rangle \rangle C \rangle$ where A is any disease indicating phrase A: {aorta, aortic, AV, AS}, B is any measurement term {gradient, velocity, area}, and C is no negation terms of the kind {no, not, without, neither, none}. Once the pattern is matched, numeric values are located following the measurement names in the same sentence that were juxtaposed with names of relevant units. An example of aortic stenosis measurement extraction is illustrated in the paragraph below.

"Aortic Valve: The aortic valve is thickened and calcified. Severe aortic stenosis is present. The aortic valve peak velocity is 6.18 m/s, the peak gradient is 152.8 mmHg, and the mean gradient is 84.9 mmHg. The aortic valve area is estimated to be 0.28 cm$^2$."

In general, the text-based aortic stenosis detection is fairly stable with very few false positives as indicated in Table 1. Only 3 errors were observed among thousands of patients after a thorough analysis of the detected cases, as listed in the third column. Table 1 illustrates the false discovery rate (FDR) of disease (AS) and measurement (peak velocity and mean gradient) detection.

TABLE 1

| | FDR | False Positives |
|---|---|---|
| AS | 2/191 | Indication/Hx: EVAL FOR MS/MR, AS/AI De-Identied AS SMOKER |
| Peak Velocity | 1/364 | aortic stenosis is present. The aortic valve peak velocity is 2.61 ⊲9 m/s, the peak gradient is 28.9 mmHg |
| Mean Gradient | 0/410 | — |

Extracting Echocardiographer Measurements

Referring to FIG. 3, an illustration is provided of measurement extraction from echocardiography screens.

Figure 3A:
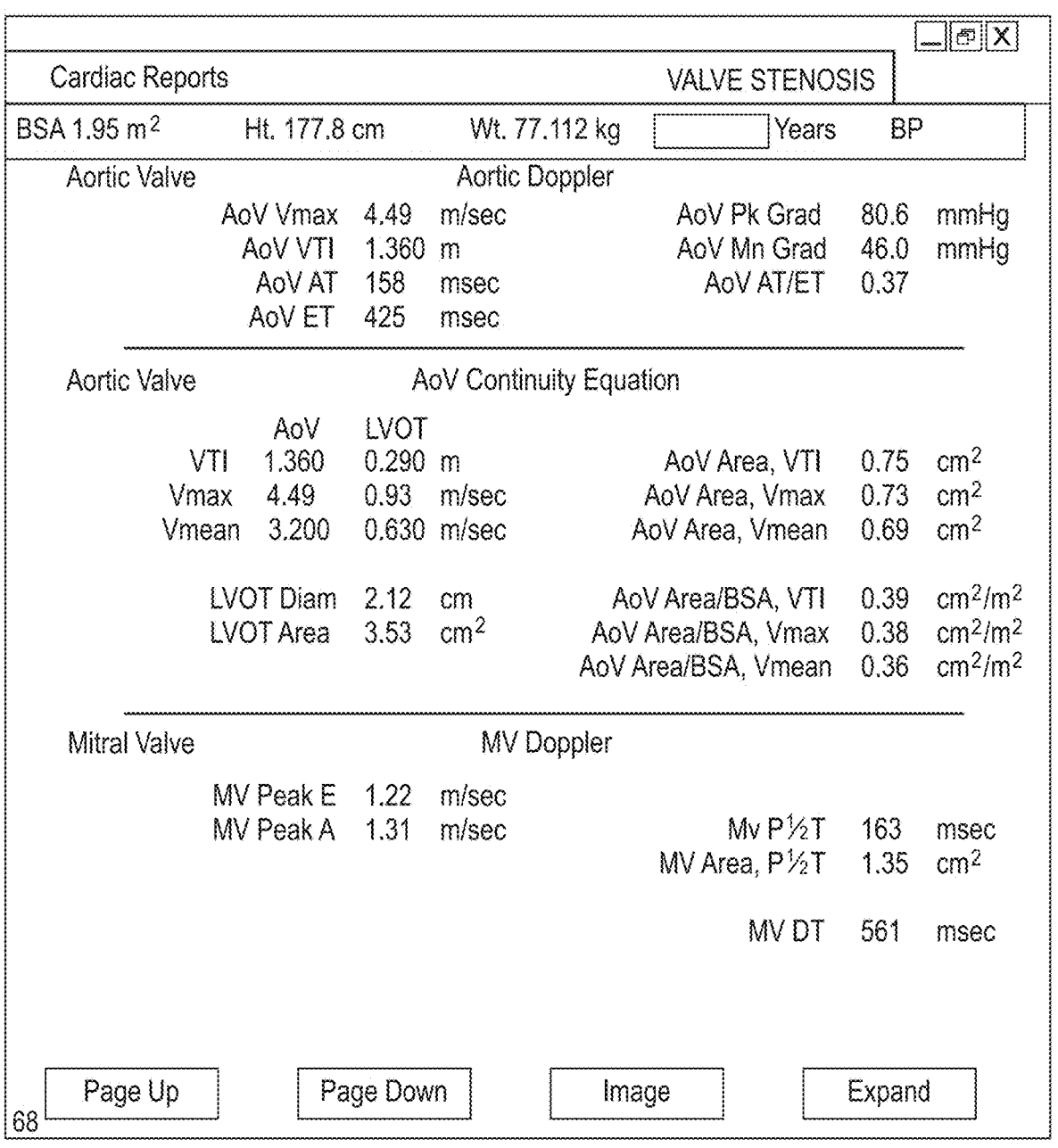
FIG. 3A is an exemplary image of an echocardiography screen having a plurality of measurements.
Figure 3B:
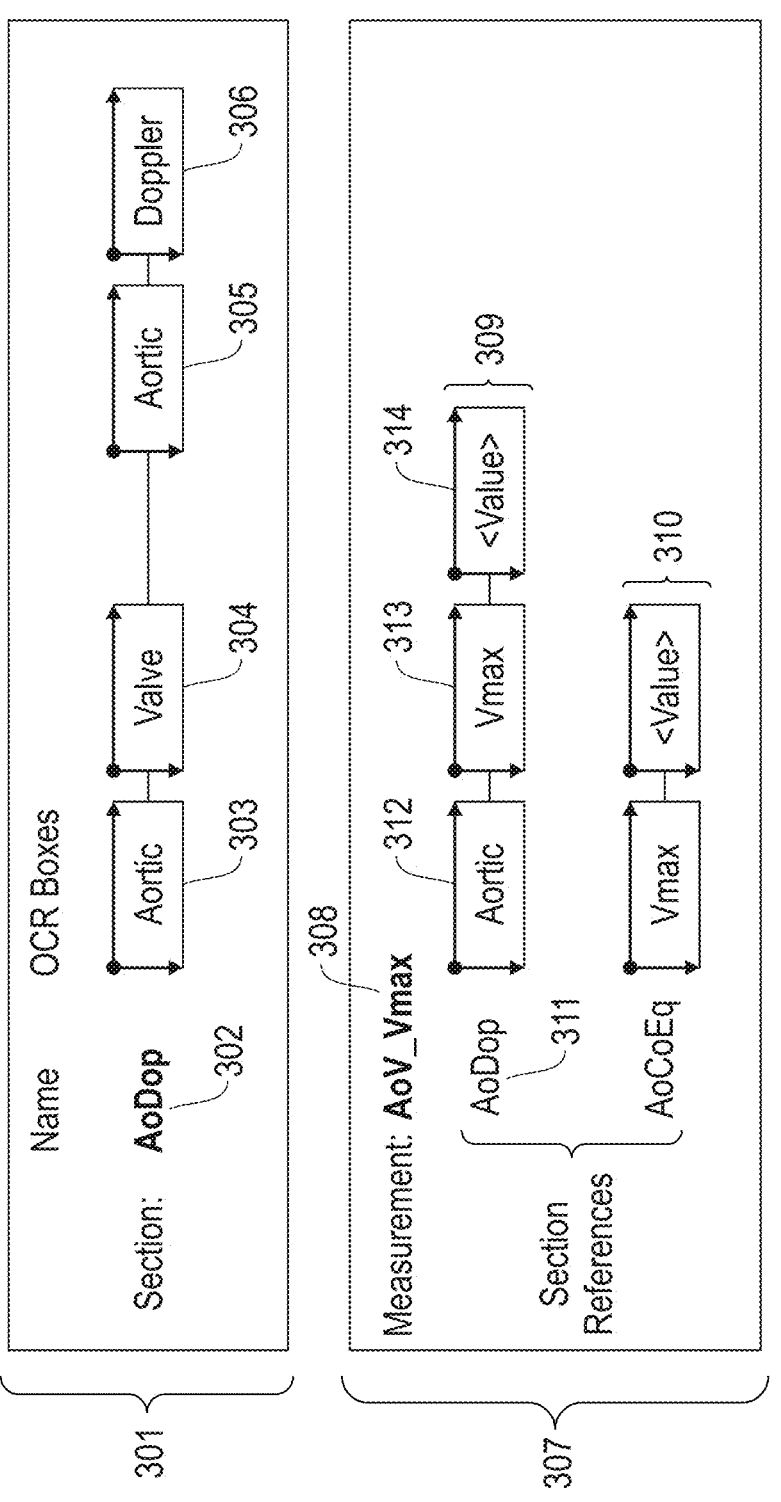
FIG. 3B illustrates exemplary templates according to embodiments of the present disclosure.

The evidence for aortic stenosis can be extracted from the measurements made by the echocardiographer captured as text-only screens such as the one shown in FIG. 3A. To extract the measurements, the frames depicting the measurements are selected. A relevant tabular template is applied to identify the semantic names of the measurements. An exemplary tabular template is shown in FIG. 3B. Section template 301 includes section name 302 and one or more OCR boxes 303 . . . 306 having a relative offset between then. Measurement template 307 includes a measurement name 308 and one or more value templates 309 . . . 310. Each value template 309 . . . 310 includes a section reference 311 (e.g., to the section of template 301) and one or more OCR boxes 312 . . . 314 having a relative offset between then.

An optical character recognition algorithm is used to extract text. In some embodiment, the DataCap OCR engine is used while in other embodiments, the Tesseract OCR engine is used. However, it will be appreciated that any number of OCR engines are suitable for use according to the present disclosure. The document layout templates of device manufacturer's screens is learned automatically. The template learning is focused per anatomical region and exploits the invariance in topological layout of the measurement name value pairs in the tabular regions. Once the templates are learned, they are matched to any given text only screen to read off the expected measurement names.

The images are processed within the text regions through an image enhancement process to increase the robustness of OCR. FIG. 3C shows the text extracted from measurement screen of FIG. 3A using this video text detection algorithm. The OCR-based measurement extraction module was tested on 114 text-only frames across 114 patients, and a total of 1719 measurements were verified. For this validation set, the system extracted 99.7% of the measurements correctly, with the remaining errors caused by the numeric values being split by the OCR engine.

Figure 4:
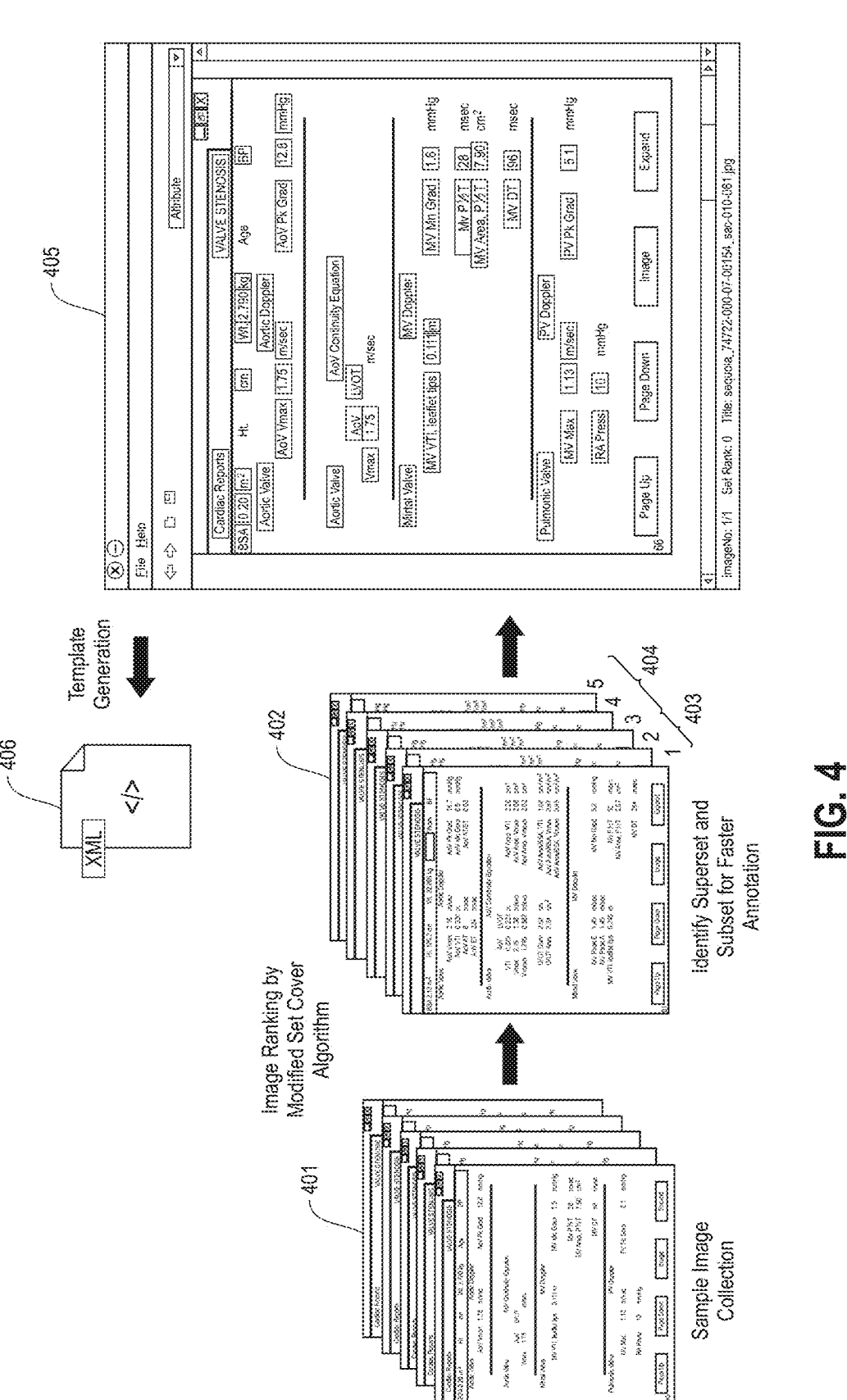
FIG. 4 illustrates a template learning phase according to embodiments of the present disclosure.

Referring to FIG. 4, a learning phase for template generation is illustrated according to embodiments of the present disclosure. A sample image collection 401, comprising a plurality of images is read. The images are ranked 402 according to the set cover algorithm set forth below. Supersets 403 and subsets 404 of images are identified to avoid duplication and thus make annotation faster. A GUI 405 is provided that displays automatic attribute-value pair suggestions based on a rule-based approach and allows input of user corrections. Based on the corrected attribute-value pairs and their layout, a template is generated 406.

According to various embodiments, the training mode takes in an initial sample of images drawn from a larger corpus of medical imagery. In some embodiments, this initial sample comprises ~100-200 randomly selected images. In addition to generating a template as set forth herein, a list of common typos is also compiled based on the OCR module output. This list is useful to supplement the knowledge base used to increases measurement accuracy. In order to simplify and speed up training, the training images are ranked for presentation to a user for verification, as discussed above. The ranking algorithm allows presentation of images with the most information to the user in the earliest stages of training. In this way, the initial determinations made by the system are reinforced. Via a user interface, a user can correct for mistakes or missed measurements. By optimizing presentation of screens for verification, a user is required to evaluate fewer images and to spend less time overall on validation and correction.

As noted above, in various embodiments, a graphical user interface is provided for training. Given a pool of new machine images N, they are clustered into k different groups G. The images are ranked based on the set cover algorithm given below. A user is presented with one or more images from each group G in combination with an initial determination, which in some embodiments is based on rule-based approach, for every measurement attribute-value-unit pair and its section header. In some embodiments, the rule based approach comprises applying predetermined templates based on vendor and device information associated with the image. For example, a given vendor may always place certain measurements at a predetermined location in a frame, while other vendors may have significant variation among product lines. Such a rule based approach is used to detect table structure to locate section names, table header, measurement names and units.

Through the UI, a user can annotate the image, i.e., by correcting misclassified pairs, removing non-relevant words, or adding user-defined naming. Subsequent images may then be updated based on the current corrections. This may reduce by half the amount of clicking in following annotations.

The above process may be repeated until all images in the training set have been annotated. Image templates of each group $G_i : t_i , \ldots , t_j$ are merged to generate a cluster-specific/ rank-specific template $T_i$. After training, the machine-specific template comprises a set of cluster-templates/rank-templates, i.e., $\ni \{T_1, \ldots, T_k\}$, which can be used to extract measurements from any test image at run time.

Figure 5:
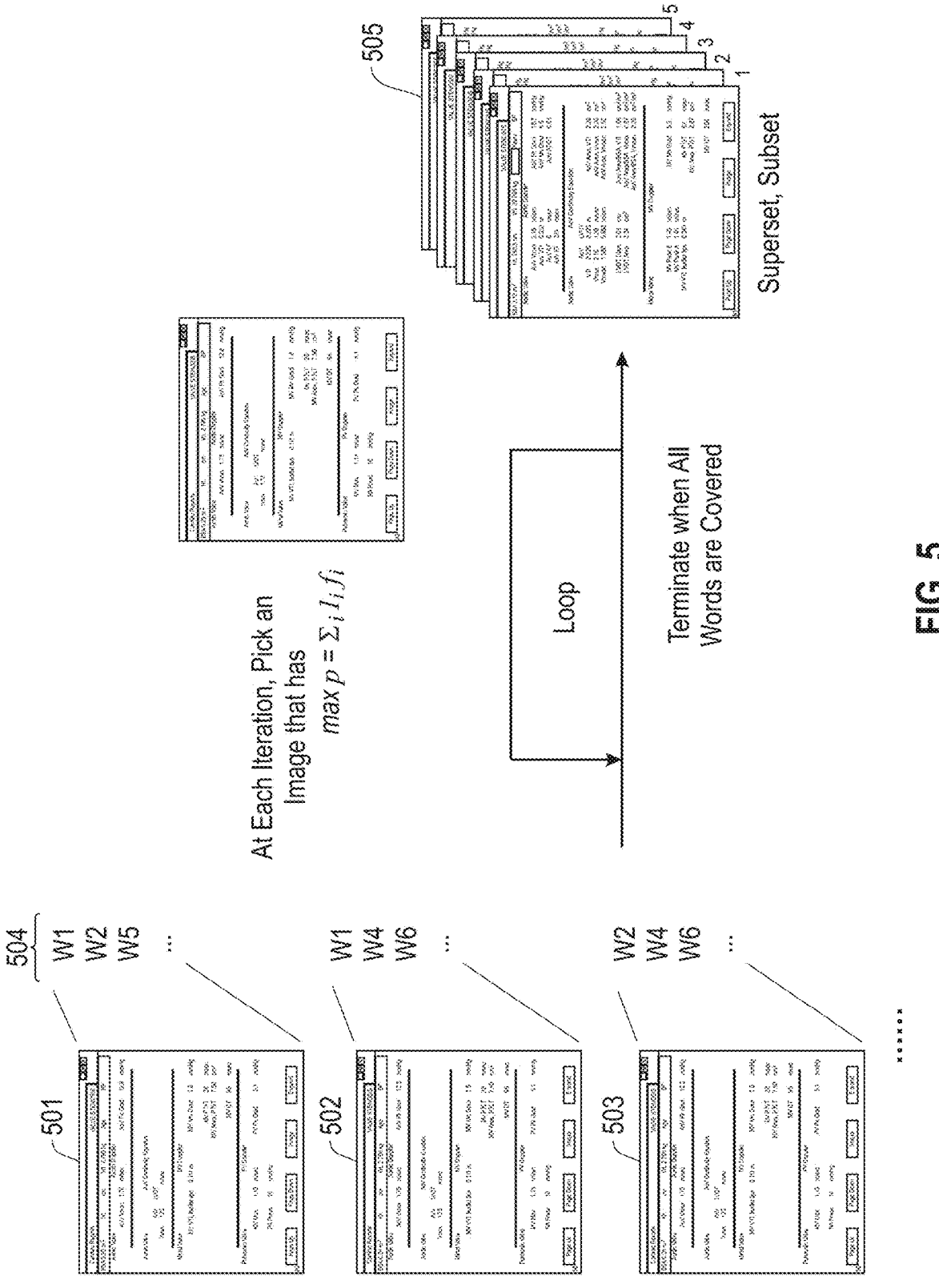
FIG. 5 illustrates a set cover algorithm according to embodiments of the present disclosure.

Referring to FIG. 5, a set cover algorithm is illustrated according to embodiments of the present disclosure. The set cover algorithm identifies a set of images (superset) that can represent all of the images (superset+subset). In each step of this greedy approach, an image is chosen to the superset that has the maximum profit as given by Equation 1, where $I_i$ is the indicator of word i and $f_i$ is the normalized frequency of word i. A plurality of images 501 . . . 503 are analyzed, each containing a plurality of words. 504. At each iteration of the algorithm, an image is picked that has maximum p. The algorithm concludes when all words are covered, yielding superset and subsets 505.

$$p = \sum_i I_i f_i, \qquad \text{Equation 1}$$

Figure 6:
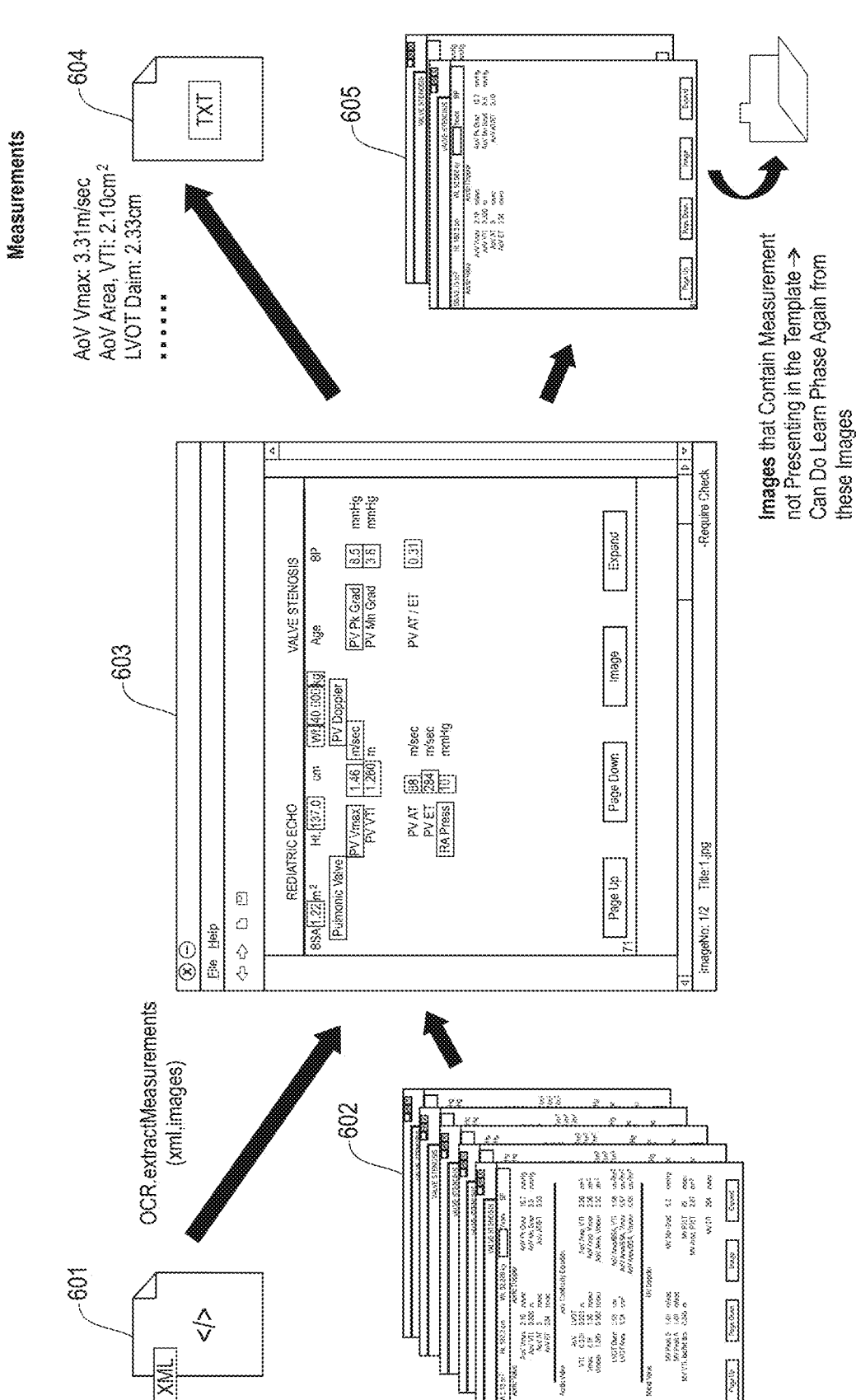
FIG. 6 illustrates a template test phase according to embodiments of the present disclosure.

Referring to FIG. 6, a measurement extraction and testing method is illustrated according to embodiments of the present disclosure. In runtime mode, systems of the present disclosure extract measurements automatically using the knowledge and the templates. Extracted text 601 and original images 602 are provided to user interface 603 for display. Based on the template, a list of measurements 604 is extracted. Images containing regions or combinations of measurements not reflected in the template 605 may be flagged and used for further training of the system.

In the runtime stage, a new image is assigned to a cluster based on a similarity score. The cluster-template is retrieved and used to extract measurements from the test image. If there is no close template, the default rule-based approach is used to extract the measurements. T is searched extensively to see if any measurements are matched to the test image. Images that need retraining will be set aside or flagged so user can rerun the training phase to create a new template from the unclassified test image.

Disease Extraction from Doppler Image Analysis

In Doppler echocardiography images, the clinically relevant region is known to be within the Doppler spectrum, contained in a rectangular region of interest as shown in FIG. 2B. To ensure the measurement extraction is attempted on relevant frames depicting the aortic valve, a classifier is provided using features derived from the region depicting Doppler patterns in images. This image region is fed to a pre-trained convolutional neural network (CNN) consisting of 5 convolution layers, two fully connected layers and a SoftMax layer with 1000 output nodes. The CNN is used as a feature generator here. Even though the CNN was trained in another imaging domain, the earlier layers of the neural network capture generic features such as edges which are also applicable in the present domain. For feature generation, a feature vector of size 4096 is harvested at the output of the first fully connected layer of the network and the images classified using a support vector machine (SVM) classifier. To train the SVM, an expert reviewed dataset of 496 CW Doppler patterns is used, each labeled with one of the four valve types. A set consisting of 100 of these images was randomly isolated as a test set. The SVM was optimized for kernel type and slack and kernel variables on the remaining 396 images using five-fold cross validation. Using the CNN derived features, the SVM achieved an accuracy of 92% across all valves with all aortic valve CW Doppler frames being labeled correctly. The tricuspid stenosis valve pattern accounted for nearly half the errors as it is similar to the aortic stenosis valve pattern.

In various embodiments, a frame of interest is read, and the mode reflected in the frame is determined in advance of valve detection. For example, a frame may reflect B-Mode, M-Mode, CW-Doppler, PW-Doppler, Text-Panel, Color-Doppler, Color-Doppler M-Mode. An frame, or a region of interest therein is provided to a pre-trained convolutional neural network (CNN). The CNN is used as a feature generator. In some embodiments, a feature vector of size 4096 is harvested at the output of the first fully connected layer of the network and the images classified using a support vector machine (SVM) classifier. To train the SVM, a dataset of imagery is used reflecting a plurality of modes, each labeled with the appropriate mode. In embodiments including mode detection, the valve detection stage may take as input the mode label. In some embodiments, multiple valve detection stages are maintained, corresponding to each possible mode label, and the image is routed to the appropriate valve detection stage according to the valve label.

Extraction of Doppler Patterns

Figure 7A:
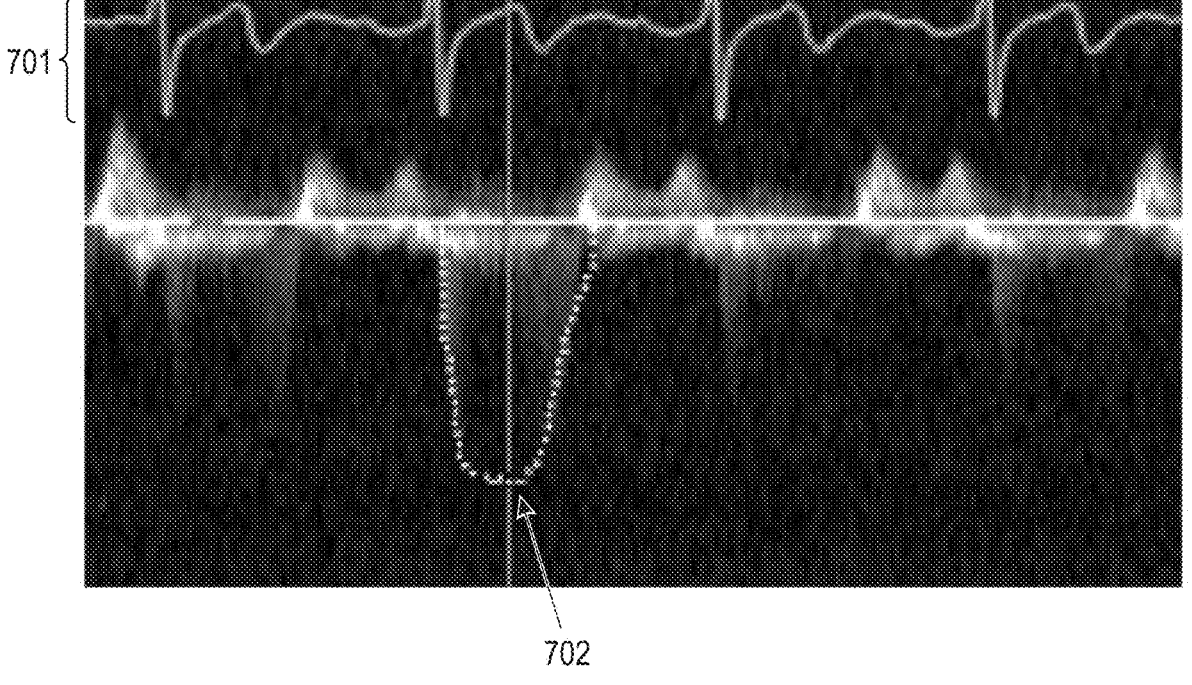
FIGS. 7A-D illustrate Doppler envelope extraction according to embodiments of the present disclosure.
Figure 7B:
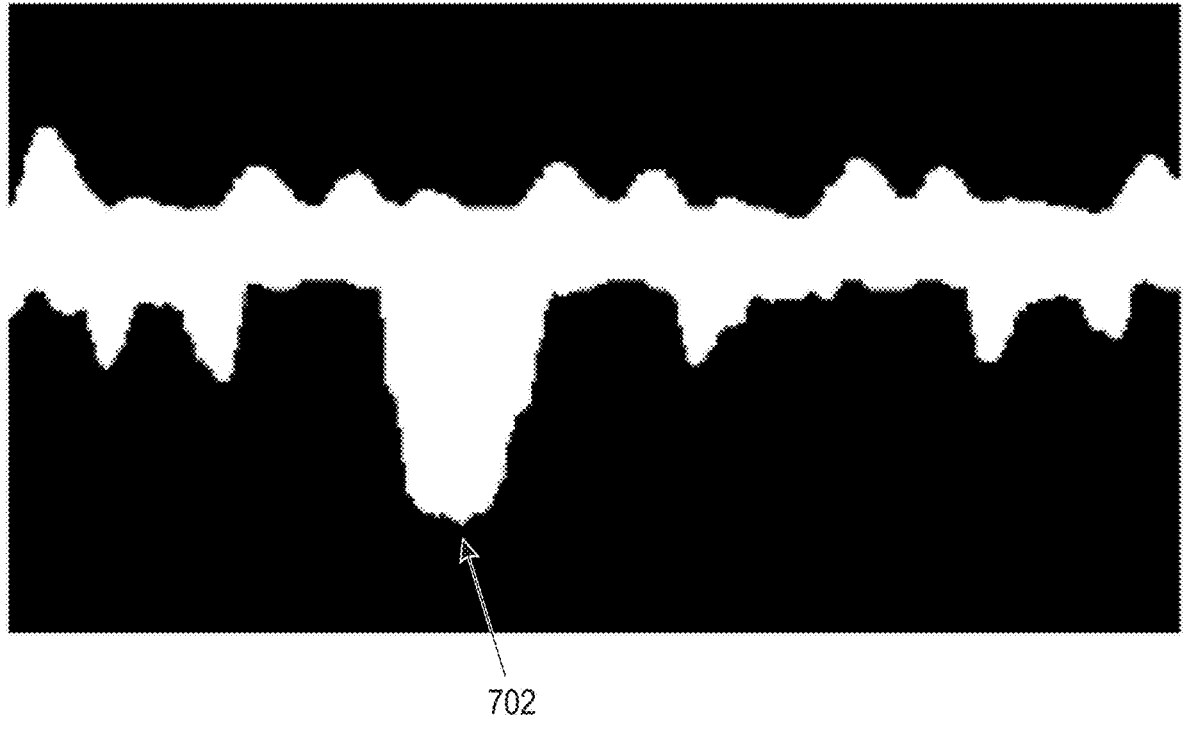
Figure 7C:
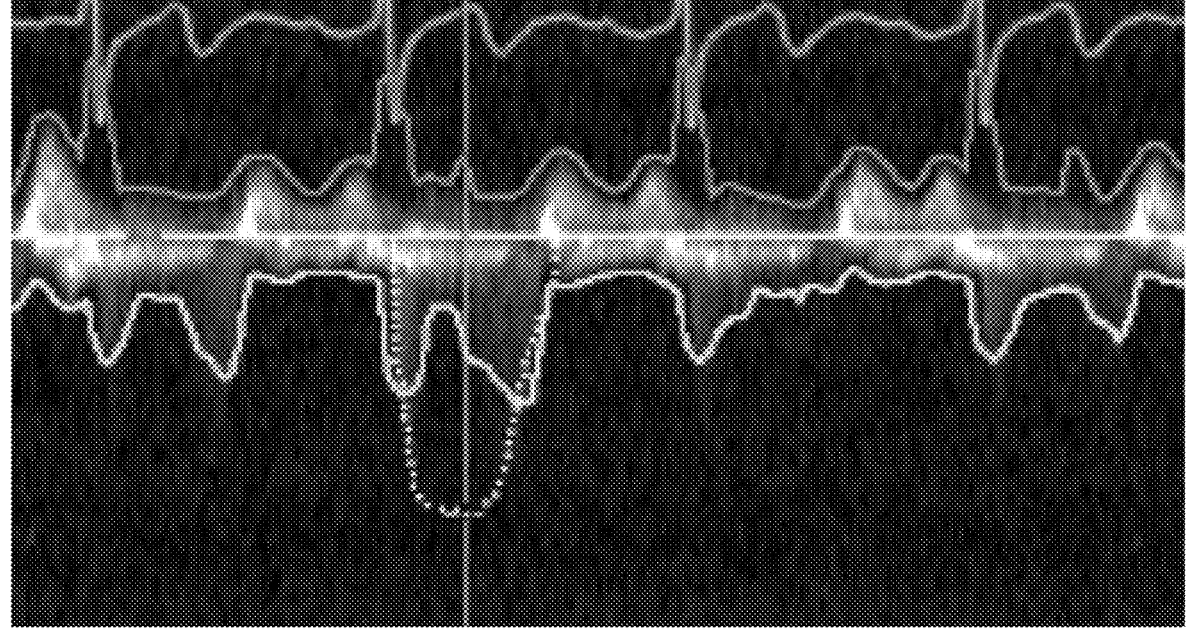
Figure 7D:
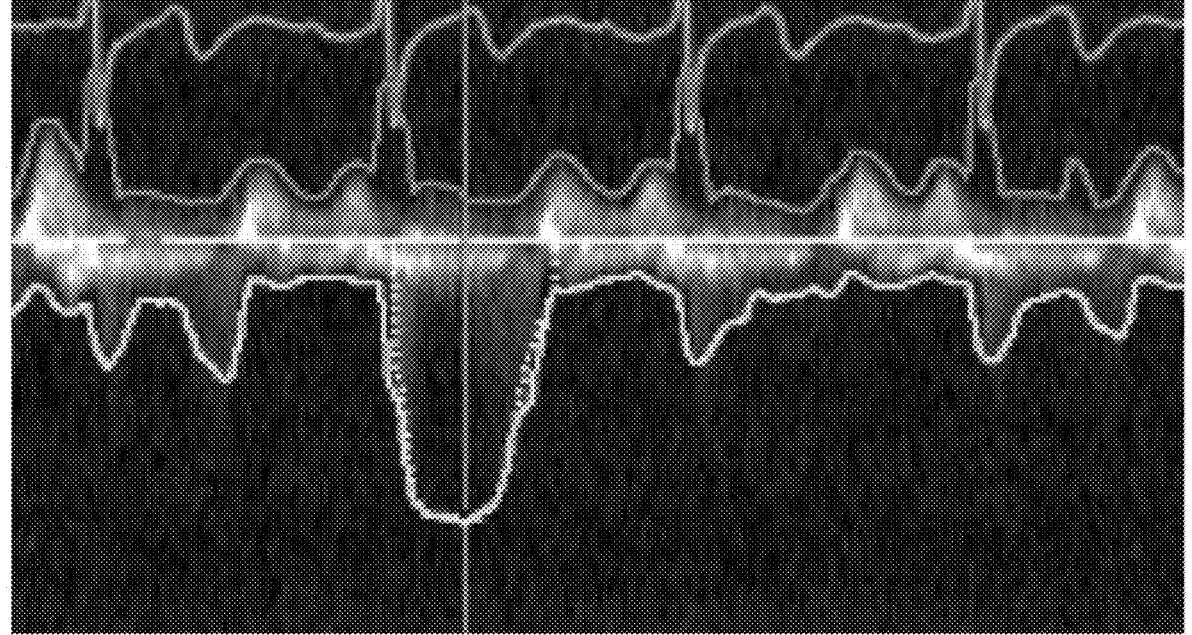

Extracting of Doppler spectrum in some embodiments uses pre-processing steps of region of interest detection, ECG extraction, and periodicity detection. In addition, various embodiments exploit the tracings of echocardiographers as shown in FIG. 7. To extract echocardiographer's envelope annotation, the calculated Doppler velocity profile 701 is excluded from the ROI. Otsu's thresholding algorithm is applied on the remaining image (as pictured in FIG. 7B) to highlight the manual delineation 702 which is connected to the baseline. Then, the extracted annotation (shown in FIG. 7C) is added to the filled up largest region (from FIG. 7B). The boundary pixels are traced as shown in FIG. 7D. The Doppler envelop extraction was tested on over 7000 images during training, and the results of the various stages of processing are indicated in Table 2.

TABLE 2

| Measurement made | Images tested | Error |
|---|---|---|
| $V_{max}$ | 1054 | 0.29 ± 0.78 m/sec |
| $M_g$ | 785 | 0.08 ± 10.05 mmHg |

Measurement Extraction from Doppler Patterns

Maximum jet velocity ($V_{max}$) is defined as the peak velocity in the negative direction for the Doppler pattern for aortic stenosis. Since the Doppler envelope traces are available, the pixel value of the negative peak in the Doppler spectra can be easily noted. To convert the imaging-based measurement to a physical velocity value, the text calibration markers on the vertical axis in the ROI are analyzed using an OCR engine to read off the velocity value. The maximum value of velocity during systole within each cycle is a candidate for the $V_{max}$. The second measurement indicative of aortic stenosis is mean pressure gradient (MPG). MPG is calculated from velocity information following the estimation in Equation 2, where N is the number of pixels within the QT interval of ECG, and V is the velocity.

$$M_g \approx \sum_V \frac{4V^2}{N} \qquad \text{Equation 2}$$

Disease Prediction Using Multimodal Learning

In some embodiments, after collecting all the measurements derived from each modality processing, a feature vector is formed as follows in Equation 3, where the 'b' is for billable diagnosis, 's' for significant problems, 't' for textual reports, 'o' for video text, and T for image analysis features. The first 3 features are binary while the rest are actual measurements made in the respective modalities. To train the predictor, a set of patients may be used with known aortic stenosis (independently validated clinically), and learn the correlation between feature values and the disease label (aortic stenosis) using a random forests learner. In some embodiments, the random forests are constructed with T trees (e.g., T=4, T=100), with each tree having a minimum node size n (e.g., n=4, n=10), and maximum depth of 10. It will be appreciated that the parameters can be tuned depending on the task of interest and the size of the available training data.

$$F_p = \{V_{1b}, V_{2s}, V_{3t}, V_{4t}, V_{5t}, V_{6o}, V_{7o}, V_{8t}, V_{9t}\} \qquad \text{Equation 3}$$

Given determination of a disease label as described above, prior studies may be surveyed to determine when such a diagnosis first occurred. In this way, gaps or discrepancies in the record may be located. When a gap or discrepancy is detected, a notification may be dispatched to a technician or other personnel such as a medical coder.

According to various embodiments, when reading a current study for a patient the past study records for that patient are processed (both reports NLP and image cognition) and compared to the current study both as prior positive findings to reconfirm and as incidental findings (e.g., a mass was seen but dismissed as benign). In some embodiments, prior inconsistent results may be included in a PACS worklist. In this manner, a re-read or review process may be triggered.

Clinical Study Results

A retrospective clinical study was conducted on a large patient data set acquired from a nearby hospital. The experimental context was to evaluate if there were missed diagnosis of aortic stenosis in their records when in fact evidence could be found from the underlying clinical data. Specifically, the analysis was restricted to patients for which 4 modalities of information were available, namely, billable diagnosis, significant problems, and echocardiogram reports and imaging studies giving rise to a total of 991 patients with 1,226 reports and 121,811 Doppler images. These studies were independently validated clinically and 395 patients were found to have aortic stenosis serving as the ground truth.

A 10 fold cross-validation was done by randomly splitting the data into 10 folds, 9 for training and 1 for testing. Table 3 shows the precision, recall, F-score, and overall accuracy of the baseline and random forests with different combinations of features, including a fusion of image and OCR features—referred to as min(I, O). Selecting the minimum of these two values gave a more conservative estimate of the severity of the disease. Out of the 395 patients manually identified by experts, 99 were newly discovered patients from our multimodal analysis giving rise to over 25% new discoveries.

Table 3 illustrates comparative performance of rule-based baseline and random forest with features extracted from structured information, reports, images, and OCR text. min (I, O) refers to the fusion of image and OCR features by taking the minimum of the two for each individual feature/ parameter.

TABLE 3

| | Features | | | | min | Performance | | | |
| --- | --- | --- | --- | --- | --- | --- | --- | --- | --- |
| | Structured | Report | Image | OCR | (I, 0) | Precision | Recall | F-score | Accuracy |
| Baseline | x | x | x | x | | 0.84 | 1.00 | 0.93 | 0.92 |
| Random | x | | | | | 1.00 | 0.53 | 0.70 | 0.81 |
| Forest | | x | | | | 0.96 | 0.55 | 0.70 | 0.81 |
| | | | x | | | 0.80 | 0.50 | 0.62 | 0.75 |
| | | | | x | | 0.94 | 0.50 | 0.66 | 0.79 |
| | | | | | x | 0.94 | 0.56 | 0.70 | 0.81 |
| | | | x | x | | 0.78 | 0.59 | 0.67 | 0.77 |
| | | x | | | x | 0.93 | 0.73 | 0.82 | 0.87 |
| | | x | x | x | | 0.82 | 0.71 | 0.77 | 0.83 |
| | x | x | | | x | 0.96 | 0.89 | 0.92 | 0.94 |
| | x | x | x | x | | 0.87 | 0.89 | 0.88 | 0.90 |

Comparison Against Baseline

The baseline was a rule-based model, which returned all patients with at least one piece of evidence from any of five sources. Here the evidence was either the presence of disease mentions or exceeding the normal ranges for $V_{max}$ and $M_g$ according to the AHA guidelines. The best-performing model was a random forest with features from all the different sources, achieving 96% precision that is 12% higher than the baseline. Combining features using random forests compensates for potential errors in individual modality detections, making its precision higher than the baseline method. The higher precision will reduce unnecessarily flagging of patients which would have otherwise have lowered the confidence in such prediction system for practical uses.

Figure 8:
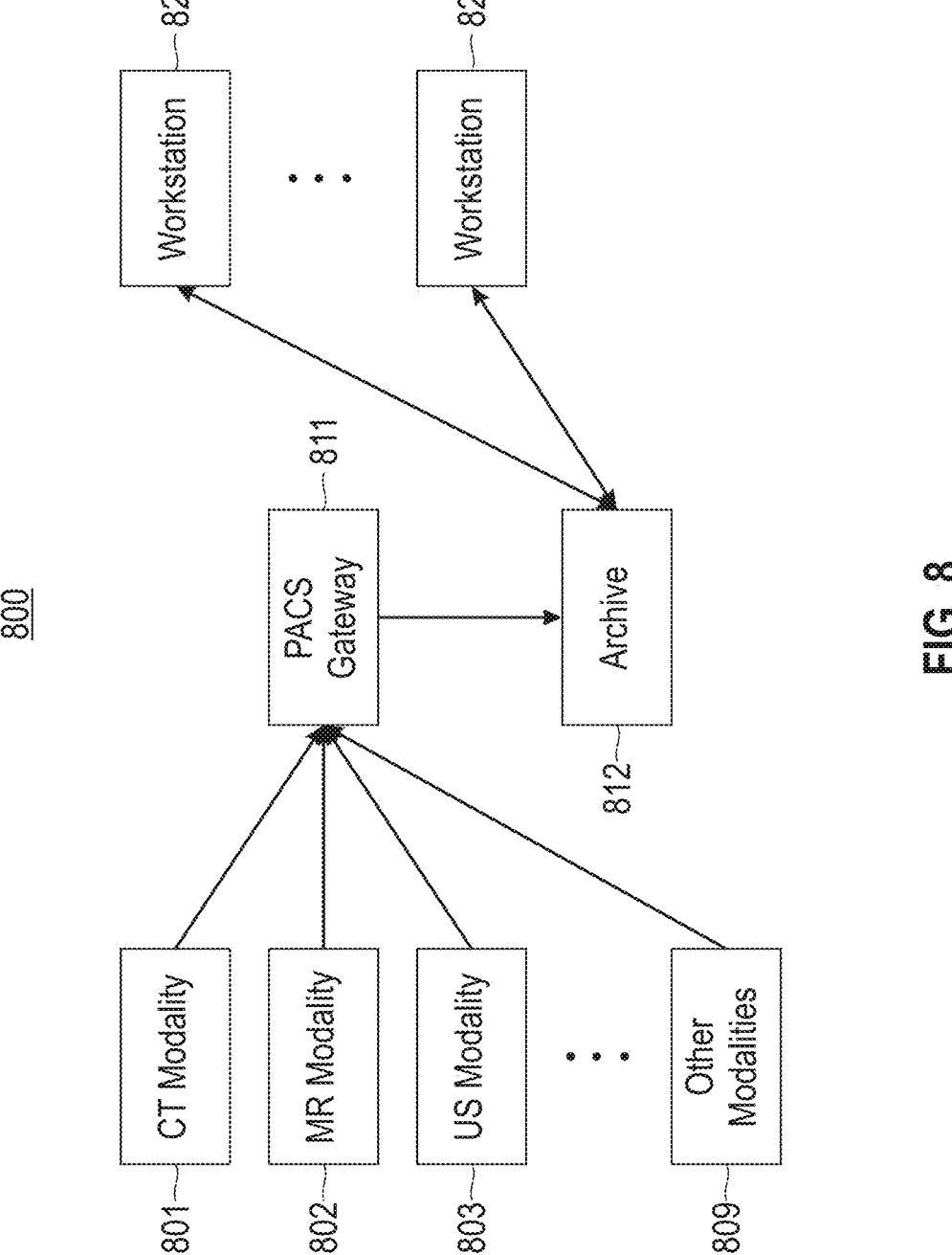
FIG. 8 depicts an exemplary Picture Archiving and Communication System.

Referring to FIG. 8, an exemplary PACS 800 consists of four major components. Various imaging modalities 801 . . . 809 such as computed tomography (CT) 801, magnetic resonance imaging (MM) 802, or ultrasound (US) 803 provide imagery to the system. In some implementations, imagery is transmitted to a PACS Gateway 811, before being stored in archive 812. Archive 812 provides for the storage and retrieval of images and reports. Workstations 821 . . . 829 provide for interpreting and reviewing images in archive 812. In some embodiments, a secured network is used for the transmission of patient information between the components of the system. In some embodiments, workstations 821 . . . 829 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 811 comprises a quality assurance (QA) workstation. The QA workstation provides a checkpoint to make sure patient demographics are correct as well as other important attributes of a study. If the study information is correct the images are passed to the archive 812 for storage. The central storage device, archive 812, stores images and in some implementations, reports, measurements and other information that resides with the images.

Once images are stored to archive 812, they may be accessed from reading workstations 821 . . . 829. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 821 . . . 829 to burn patient studies for distribution to patients or referring physicians.

In some implementations, a PACS includes web-based interfaces for workstations 821 . . . 829. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 9:
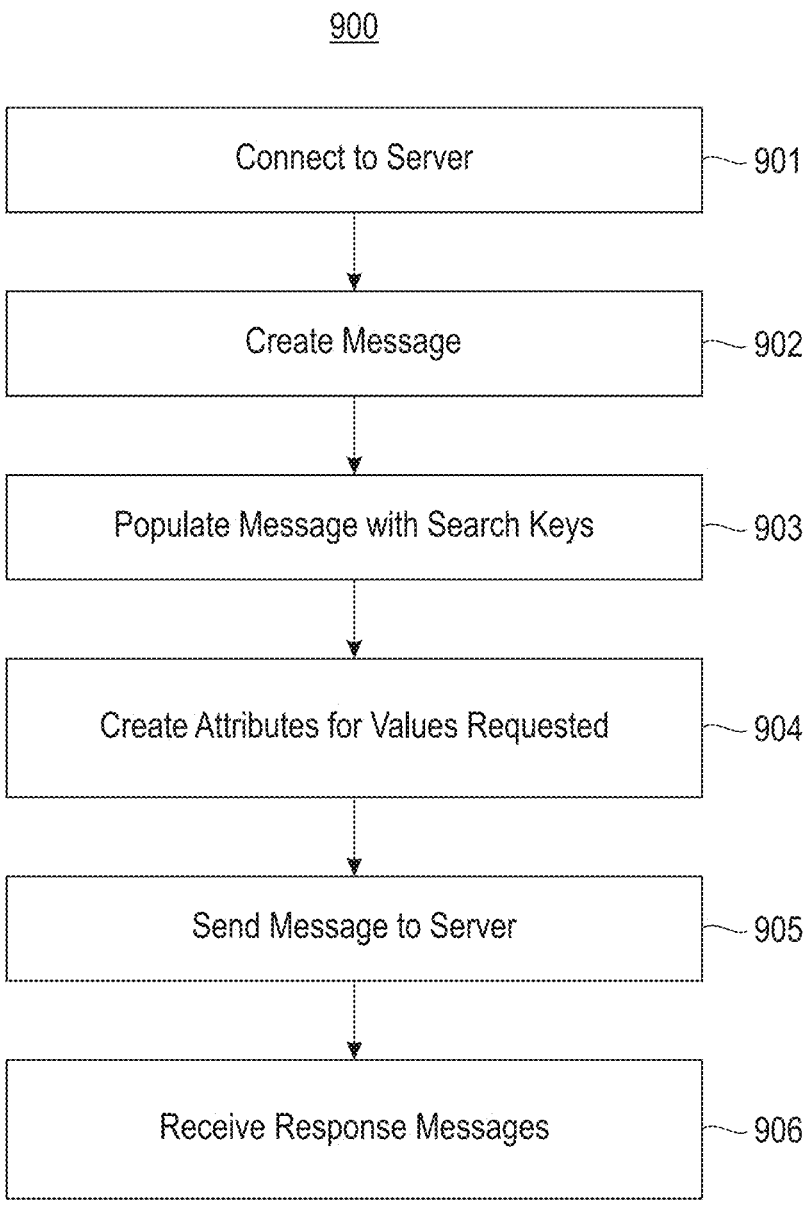
FIG. 9 illustrates an exemplary clinical image search and retrieval method.

Referring to FIG. 9, an exemplary PACS image search and retrieval method 900 is depicted. Communication with a PACS server, such as archive 812, is done through DICOM messages that that contain attributes tailored to each request. At 901, a client, such as workstation 821, establishes a network connection to a PACS server. At 902, the client prepares a DICOM message, which may be a C-FIND, C-MOVE, C-GET, or C-STORE request. At 903, the client fills in the DICOM message with the keys that should be matched. For example, to search by patient ID, a patient ID attribute is included. At 904, the client creates empty attributes for all the values that are being requested from the server. For example, if the client is requesting an image ID suitable for future retrieval of an image, it include an empty attribute for an image ID in the message. At 905, the client send the message to the server. At 906, the server sends back to the client a list of one or more response messages, each of which includes a list of DICOM attributes, populated with values for each match.

Figure 10:
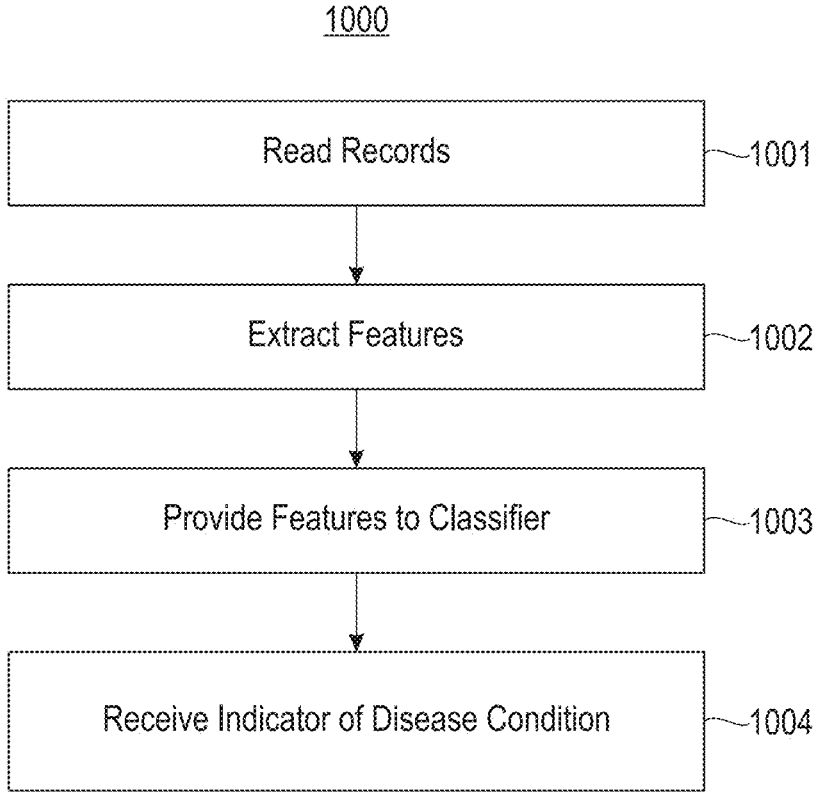
FIG. 10 illustrates a method of disease detection from multimodal data according to embodiments of the present disclosure.

Referring to FIG. 10, a method of disease detection from multimodal data is illustrated according to embodiments of the present disclosure. At 1001, a plurality of patient records associated with a patient are read from a plurality of data sources. At 1002, a plurality of disease-specific features are extracted from the plurality of patient records. At 1003, the plurality of disease-specific features are provided to a classifier. At 1004, an indicator of a likely disease condition of the patient is received from the classifier.

Figure 11:
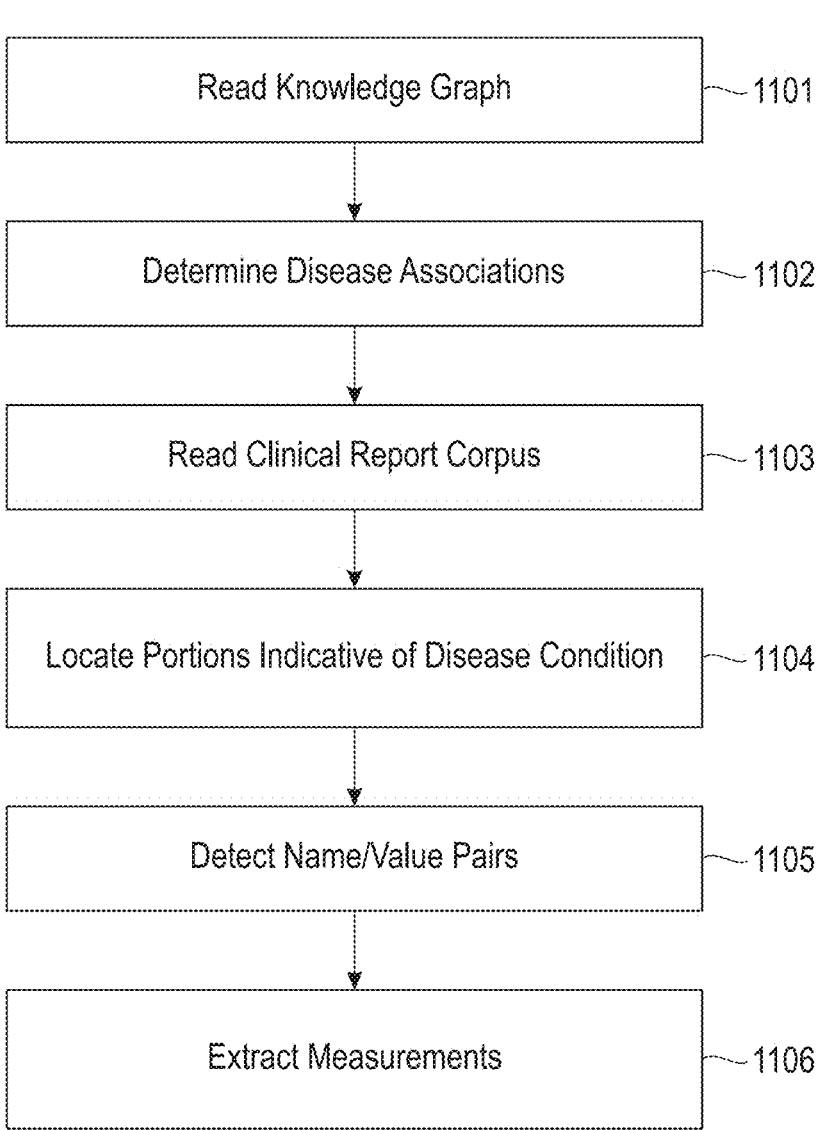
FIG. 11 illustrates a method of detection of disease from textual descriptions according to embodiments of the present disclosure.

Referring to FIG. 11, a method of detection of disease from textual descriptions is illustrated according to embodiments of the present disclosure. A knowledge graph is used to detect clinically meaningful concepts. In various embodiments, the knowledge graph models a plurality of associations between disease names, symptoms, anatomical abnormalities, and qualifiers based on phrase vocabularies from UMLS and custom vocabulary sources. At 1101, a knowledge graph of clinical concepts is read. At 1102, based on the knowledge graph, a plurality of associations are determined between disease names, symptoms, anatomical abnormalities, and qualifiers. At 1103, a corpus of clinical reports is read. At 1104, based on the plurality of associations, a plurality of portions indicative of a disease condition are located within the corpus of clinical reports. At 1105, name/value pairs are detected within each of the plurality of portions corresponding to measurements indicative of the disease condition. The disease condition is also captured in the knowledge graph. At 1106, the measurements indicative of the disease condition are extracted.

Figure 12:
FIG. 12 illustrates a method of extracting measurements from medical imagery according to embodiments of the present disclosure.
Figure 12:
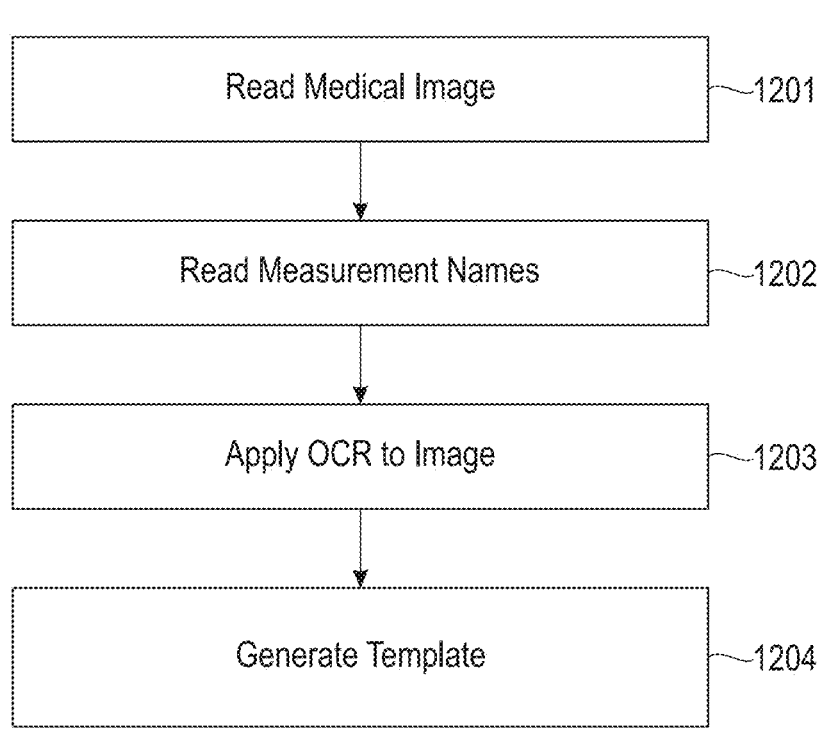

Referring to FIG. 12, a method of extracting measurements from medical imagery is illustrated according to embodiments of the present disclosure. The text layout regions within medical images are clustered to learn tabular layout of text. At 1201, a first medical image containing embedded text is read. At 1202, a plurality of measurement names are read. At 1203, optical character recognition is applied to the first medical image to locate the plurality of measurement names within the medical image. At 1204, from the locations of the plurality of measurement names within the first medical image, a tabular template is generated indicative of a layout of measurement name/value pairs. Disease-specific measurement names are captured in a measurement vocabulary and indexed by the target disease. The candidate measurement-value pairs may then be stored as disease-indicating features.

Figure 13:
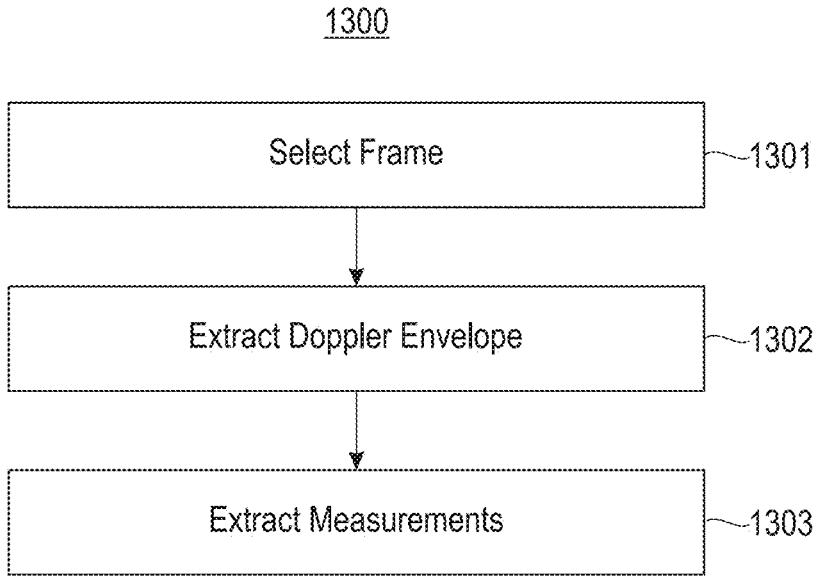
FIG. 13 illustrates a method of extraction of measurements from Doppler waveforms according to embodiments of the present disclosure.

Referring to FIG. 13, a method of extraction of measurements from Doppler waveforms is illustrated according to embodiments of the present disclosure. At 1301, a frame is selected from a medical video. The selected frame depicts a valve of interest. At 1302, a Doppler envelope is extracted from the selected frame. At 1303, based on the frame and the Doppler envelope, one or more measurements indicative of a disease condition are extracted.

Figure 14:
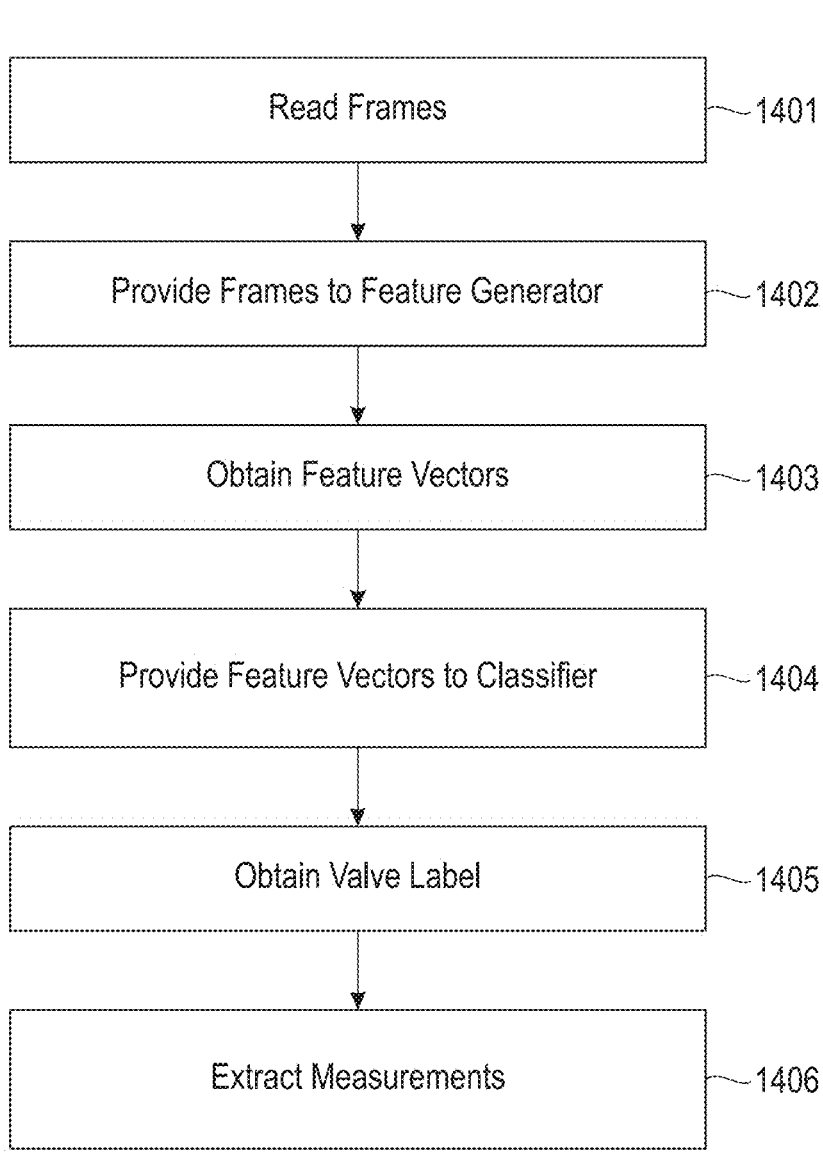
FIG. 14 illustrates a method of automatic Doppler measurement according to embodiments of the present disclosure.

Referring to FIG. 14, a method of automatic Doppler measurement is illustrated according to embodiments of the present disclosure. At 1401, a plurality of frames of a medical video are read. In some embodiments, a mode label indicative of a mode of each of the plurality of frames is determined. At 1402, each of the plurality of frames is provided to a trained feature generator. At 1403, a plurality of feature vectors corresponding to the plurality of frames is obtained from the trained feature generator. At 1404, the plurality of feature vectors is provided to a trained classifier. At 1405, a valve label indicative of a valve corresponding to each of the plurality of frames is obtained from the trained classifier. At 1406, one or more measurement indicative of a disease condition is extracted from those of the plurality of frames matching a predetermined valve label.

In various embodiments, determining the mode label includes providing the plurality of frames to a second trained feature generator. A plurality of feature vectors corresponding to the plurality of frames are obtained from the second trained feature generator. The plurality of feature vectors is provided to a second trained classifier. The mode label is obtained from the second trained classifier. In such embodiments, a set of features discriminating between mode labels are learned by the classifier, which may be a deep learning network, using a set of prior chosen training images. These features are then extracted from incoming images and then classified.

In various embodiments, an incoming imaging study is processed to first select frames depicting CW Doppler pattern. A plurality of frames of a medical video are read. A mode label indicative of a mode of each of the plurality of frames is determined. A set of features discriminating between mode labels are learned using a deep learning network using a set of prior chosen training images. These features are then extracted from incoming images and classified. The images classified into CW Doppler mode labels are then retained. From among the frames depicting CW Doppler patterns, a set of frames are selected that depict the valve of interest. A region of interest is extracted in each CW Doppler image and features discriminating between different heart valves are then learned using another deep learning network using prior chosen training CW Doppler images. New CW Doppler images are classified using the learned network and those images that are classified as containing the target valve of interest are retained. A Doppler envelope is then extracted from the selected frame. Based on the frame and the Doppler envelope, one or more measurements is indicative is extracted indicative of a disease condition from those of the at least one of the plurality of frames matching a predetermined valve label.

Figure 15:
FIG. 15 illustrates a method of discrepancy detection in medical data according to embodiments of the present disclosure.
Figure 15:
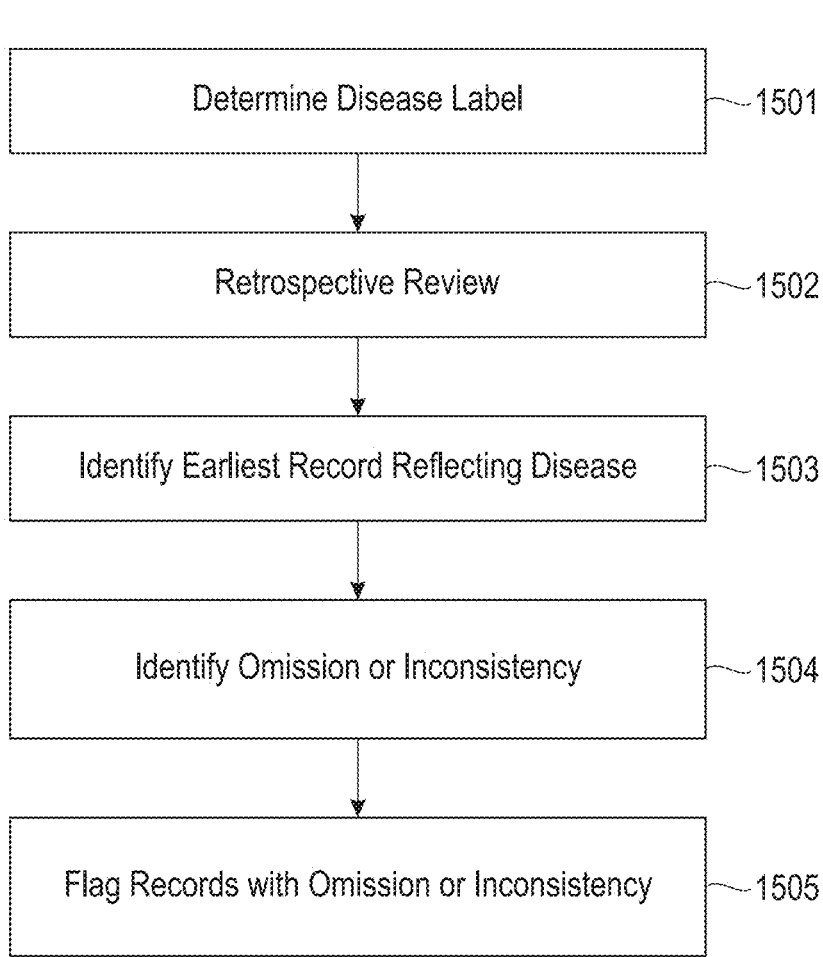

Referring to FIG. 15, a method of discrepancy detection in medical data is illustrated according to embodiments of the present disclosure. At 1501, a disease label is determined, indicative of a disease condition. In some embodiments, the disease label corresponds to a present study. At 1502, retrospective review of a plurality of electronic medical records is performed. The retrospective review comprises searching for electronic medical records relevant to the disease condition. At 1503, the earliest electronic medical record reflecting the disease condition is identified. At 1504, based on the earliest electronic medical record reflecting the disease condition, one or more of the electronic medical records having an omission or inconsistency is identified. At 1505, the one or more of the electronic medical records having an omission or inconsistency are flagged for supplemental review in a worklist.

In various embodiments, retrospective review includes searching for electronic medical records relevant to the disease condition. This includes problem list and recorded diagnosis, clinical reports and imaging studies. Given a target disease for whom the discrepancy needs to be detected, and a time period over which the discrepancy needs to be detected, a set of encounters are selected from the patient records corresponding to the specified time period. The imaging studies, and their associated reports are then drawn. The problem list and recorded diagnosis associated with these encounters are drawn. The disease mention in the problem list and recorded diagnosis is noted. Disease-specific features are extracted from imaging studies and reports. The disease specific features along with indications for the disease from problem lists are fed to the classifier to predict patients that are likely to have the disease. From the list of patients identified by the predictor classifier, their encounter records are now analyzed for discrepancy. Evidence from each step in the workflow is compared to the next step with respect to the indications for the disease. In spotting a discrepancy the positive occurrence of disease mention is used. Similarly in spotting a discrepancy in modality data (imaging), established guidelines for exceeding the values for normal ranges of measurements are utilized. The order of analysis of discrepancy in the workflow begins with the earliest evidence in imaging, then to technician measurements embedded in imaging, followed by imaging reports and then problem list and finally the recorded diagnosis in the system. With this order, the earliest place in the electronic medical record where this discrepancy has occurred is noted. The definition of a discrepancy is simply that the earlier stage in the workflow says 'yes' to the disease while the next consecutive stage in the workflow says 'no'.

Figure 16:
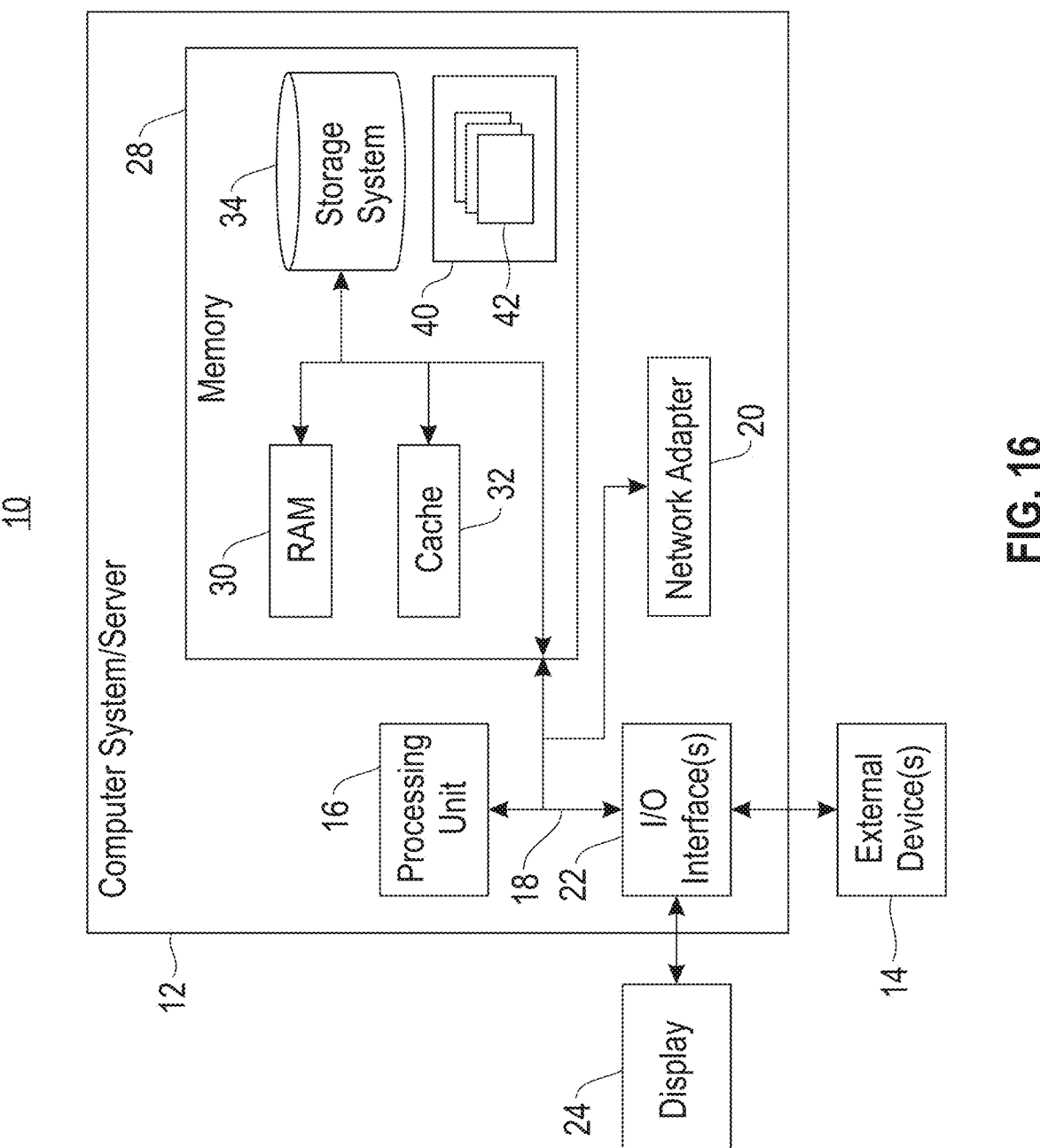
FIG. 16 depicts a computing node according to an embodiment of the present invention.

Referring now to FIG. 16, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 16, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12;

and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:

reading a plurality of frames of an ultrasound video, wherein each frame of the ultrasound video comprises a Doppler pattern;

providing at least one of the plurality of frames to a trained feature generator comprising a convolutional neural network, the convolutional neural network trained using images from an imaging domain other than Doppler echocardiography, the convolutional neural network comprising a plurality of layers, the plurality of layers comprising a first fully-connected layer and an output layer comprising a plurality of output nodes;

obtaining from the trained feature generator at least one feature vector corresponding to the at least one of the plurality of frames, wherein the at least one feature vector is obtained from the first fully-connected layer of the convolutional neural network, the at least one feature vector representing features applicable in Doppler echocardiography and the imaging domain other than Doppler echocardiography;

determining an ultrasound mode label indicative of an ultrasound mode for each of the plurality of frames;

selecting one of a plurality of valve detection stages according to the ultrasound mode label, the selected valve detection stage comprising a trained classifier;

providing the at least one feature vector to the trained classifier;

obtaining from the trained classifier a valve label indicative of a valve represented in the at least one of the plurality of frames;

based on the obtained valve label, determining whether aortic stenosis is present; and based on the determination, treating the aortic stenosis with one or more transcatheter valve replacements.

2. The method of claim 1, wherein the at least one feature vector comprises generic features applicable to multiple imaging domains including Doppler echocardiography images.

3. The method of claim 1, wherein the plurality of layers further comprises five convolutional layers, two fully-connected layers, and a Softmax layer.

4. The method of claim 1, wherein the at least one feature vector has a size of 4096.

5. The method of claim 1, wherein providing the at least one of the plurality of frames to the trained feature generator comprises providing only a region of each frame depicting Doppler patterns.

6. The method of claim 1, further comprising extracting one or more measurement derived from the Doppler pattern from the at least one of the plurality of frames, wherein determining whether a disease condition is present is further based on the one or more measurement.

7. The method of claim 6, wherein the one or more measurement comprises maximum jet velocity or mean pressure gradient.

8. The method of claim 1, wherein the trained classifier is a support vector machine.

9. The method of claim 1, wherein the valve label corresponds to the aortic valve, tricuspid valve, pulmonary valve, or mitral valve.

10. The method of claim 1, wherein the mode label corresponds to B-Mode, M-Mode, CW-Doppler, PW-Doppler, Text-Panel, Color-Doppler, or Color-Doppler M-Mode.

11. The method of claim 1, wherein determining the mode label comprises:

providing the plurality of frames to a second trained feature generator;

obtaining from the second trained feature generator a plurality of feature vectors corresponding to the plurality of frames;

providing the plurality of feature vectors to a second trained classifier; and obtaining from the second trained classifier the mode label.

12. The method of claim 11, wherein the second trained feature generator comprises a convolutional neural network.

13. The method of claim 11, wherein the second trained classifier is a support vector machine.

14. A computer program product for generating feature vector representations of Doppler echocardiography frames, the computer program product comprising a computer readable storage medium having program instructions embodied therewith, the program instructions executable by a processor to cause the processor to perform a method comprising:

reading a plurality of frames of a medical video, wherein each frame of the medical video comprises a Doppler pattern;

providing at least one of the plurality of frames to a trained feature generator comprising a convolutional neural network, the convolutional neural network trained using images from an imaging domain other than Doppler echocardiography, the convolutional neural network comprising a plurality of layers, the plurality of layers comprising a first fully-connected layer and a output layer comprising a plurality of output nodes;

obtaining from the trained feature generator at least one feature vector corresponding to the at least one of the plurality of frames, wherein the at least one feature vector is obtained from the first fully-connected layer of the convolutional neural network, the at least one feature vector representing features applicable in Doppler echocardiography and the imaging domain other than Doppler echocardiography;

determining an ultrasound mode label indicative of an ultrasound mode for each of the plurality of frames;

selecting one of a plurality of valve detection stages according to the ultrasound mode label, the selected valve detection stage comprising a trained classifier;

providing the at least one feature vector to the trained classifier;

obtaining from the trained classifier a valve label indicative of a valve represented in the at least one of the plurality of frames;

based on the obtained valve label, determining whether aortic stenosis is present; and based on the determination, treating the aortic stenosis with one or more transcatheter aortic valve replacements.

15. A system comprising:

a medical imaging records database;

a computing node comprising a computer readable storage medium having program instructions embodied therewith, the program instructions executable by a processor to cause the processor to perform a method comprising:

reading a plurality of frames of a medical video from the medical imaging records database, wherein each frame of the medical video comprises a Doppler pattern;

providing at least one of the plurality of frames to a trained feature generator comprising a convolutional neural network, the convolutional neural network trained using images from an imaging domain other than Doppler echocardiography, the convolutional neural network comprising a plurality of layers, the plurality of layers comprising a first fully-connected layer and a output layer comprising a plurality of output nodes;

obtaining from the trained feature generator at least one feature vector corresponding to the at least one of the plurality of frames, wherein the at least one feature vector is obtained from the first fully-connected layer of the convolutional neural network, the at least one feature vector representing features applicable in Doppler echocardiography and the imaging domain other than Doppler echocardiography;

determining an ultrasound mode label indicative of an ultrasound mode for each of the plurality of frames;

selecting one of a plurality of valve detection stages according to the ultrasound mode label, the selected valve detection stage comprising a trained classifier;

providing the at least one feature vector to the trained classifier;

obtaining from the trained classifier a valve label indicative of a valve represented in the at least one of the plurality of frames;

based on the obtained valve label, determining whether aortic stenosis is present; and based on the determination, treating the aortic stenosis with one or more transcatheter aortic valve replacements.

* * * * *